(12) United States Patent
Tanaka et al.

(10) Patent No.: US 8,815,485 B2
(45) Date of Patent: Aug. 26, 2014

(54) AZO COMPOUND, PIGMENT DISPERSANT CONTAINING THE AZO COMPOUND, PIGMENT COMPOSITION, PIGMENT DISPERSION, AND TONER

(75) Inventors: Masatake Tanaka, Yokohama (JP); Masashi Kawamura, Yokohama (JP); Yuki Hasegawa, Yokohama (JP); Takayuki Toyoda, Yokohama (JP); Yasuaki Murai, Kawasaki (JP); Masashi Hirose, Machida (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/812,072

(22) PCT Filed: Aug. 11, 2011

(86) PCT No.: PCT/JP2011/068643
§ 371 (c)(1),
(2), (4) Date: Jan. 24, 2013

(87) PCT Pub. No.: WO2012/026378
PCT Pub. Date: Mar. 1, 2012

(65) Prior Publication Data
US 2013/0122413 A1    May 16, 2013

(30) Foreign Application Priority Data

Aug. 27, 2010   (JP) .................................. 2010-190238

(51) Int. Cl.
  *G03G 9/09* (2006.01)
(52) U.S. Cl.
  USPC ........ 430/108.23; 534/643; 534/748; 564/86; 564/163; 106/496
(58) Field of Classification Search
  CPC .. C07C 243/22; C07C 251/78; C09B 33/153; C09B 67/0046; G03G 9/091; G03G 9/0912; G03G 9/0924
  USPC ......... 430/108.23; 534/643, 748; 564/86, 163
  See application file for complete search history.

(56) References Cited

U.S. PATENT DOCUMENTS

| | | | | |
|---|---|---|---|---|
| 3,872,078 | A | * | 3/1975 | Cseh et al. ............ 534/748 |
| 4,003,886 | A | * | 1/1977 | Muller .................. 534/575 |
| 4,062,838 | A | * | 12/1977 | Cseh et al. ............ 534/748 |
| 4,070,353 | A | * | 1/1978 | Cseh et al. ............ 534/748 |
| 4,946,948 | A | | 8/1990 | Hari et al. |
| 5,559,216 | A | * | 9/1996 | Jung et al. ............ 106/31.75 |
| 6,099,631 | A | | 8/2000 | Tregub et al. |
| 7,384,472 | B2 | | 6/2008 | Schweikart et al. |
| 2007/0125263 | A1 | * | 6/2007 | Weber et al. ........... 106/31.81 |
| 2007/0215008 | A1 | * | 9/2007 | Schweikart et al. ...... 106/496 |
| 2009/0005474 | A1 | * | 1/2009 | Jaunky et al. .......... 524/89 |
| 2009/0101874 | A1 | * | 4/2009 | Weber et al. ........... 252/586 |
| 2010/0273101 | A1 | * | 10/2010 | Tani et al. ............ 430/108.23 |
| 2013/0130164 | A1 | | 5/2013 | Murai et al. |

FOREIGN PATENT DOCUMENTS

| | | | |
|---|---|---|---|
| CS | 246533 B1 | * | 12/1987 |
| FR | 2106450 A1 | | 5/1972 |
| JP | 56-166266 A | | 12/1981 |
| JP | 1-306475 A | | 12/1989 |
| JP | 2002-504586 A | | 2/2002 |
| JP | 2007-262382 A | | 10/2007 |
| WO | 2009/060886 A1 | | 5/2009 |
| WO | 2012/026504 A1 | | 3/2012 |
| WO | 2013/054938 A1 | | 4/2013 |

OTHER PUBLICATIONS

Diamond, Arthur S & David Weiss (eds.) Handbook of Imaging Materials, 2nd ed.. New York: Marcel-Dekker, Inc. (Nov. 2001) pp. 178-182.*
Chemical Abstracts 109:130807 (2013).*
English language translation of CS 246533 (Dec. 1987).*
Datta E. Ponde et al., "Selective Catalytic Transesterification, Transthiolesterification, and Protection of Carbonyl Compounds over Natural Kaolinitic Clay" 63 (4) J. Org. Chem. 1058-1063 (Jan. 1998).
Kiran Kumar Solingapuram Sai et al., "Knorr Cyclizations and Distonic Superelectrophiles," 72 (25) J. Org. Chem. 9761-9764 (Nov. 2007).

(Continued)

*Primary Examiner* — Christopher Rodee
(74) *Attorney, Agent, or Firm* — Fitzpatrick, Cella, Harper & Scinto

(57) ABSTRACT

A compound that can improve azo pigment dispersibility in a non-water-soluble solvent. The compound is represented by formula (1):

(1)

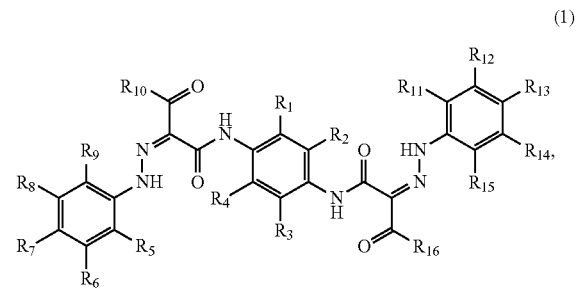

wherein $R_1$ to $R_4$ represent hydrogen or halogen; $R_5$ to $R_9$ represent hydrogen, $COOR_{17}$ or $CONR_{18}R_{19}$, and at least one of $R_5$ to $R_9$ represents $COOR_{17}$ or $CONR_{18}R_{19}$, where $R_{17}$ to $R_{19}$ represent hydrogen or an alkyl group having 1 to 3 carbons; $R_{10}$ represents an alkyl group having 1 to 6 carbons or a phenyl group; $R_{11}$ to $R_{15}$ represent a hydrogen, $L_1R_{20}$ or $L_2R_{21}R_{22}$, and at least one of $R_{11}$ to $R_{15}$ represents $L_1R_{20}$ or $L_2R_{21}R_{22}$, where $L_1$ represents a divalent linking group, $L_2$ represents a trivalent linking group, and $R_{20}$ to $R_{22}$ represent an alkyl group having 8 or more carbons or an alkenyl group having 8 or more carbons; and $R_{16}$ represents an alkyl group having 1 to 6 carbons or a phenyl group.

11 Claims, 2 Drawing Sheets

(56) References Cited

OTHER PUBLICATIONS

John C. Sheehan et al., "Notes—A Convenient Synthesis of Water-Soluble Carbodiimides," 26 (7) J. Org. Chem. 2525-2528 (Jul. 1961).

Norman O. V. Sonntag, "The Reaction of Aliphatic Acid Chlorides," 52 (2) Chemical Reviews 237-416 (1953).

Melvin S. Newman et al., "N-Methylpyrrolidone as Solvent for Reaction of Aryl Halides with Cuprous Cyanide", 26 (7) J. Org. Chem. 2525 (Jul. 1961).

"Experimental Chemistry Course," Maruzen, First Edition, vol. 19, p. 176-188 (Maruzen Publishing Co., Ltd. 1957).

"Experimental Chemistry Course," Second Edition, vol. 17-2, p. 162-179 (Maruzen Publishing Co., Ltd. 1956).

"New Experimental Chemistry Course," First Edition, vol. 15, p. 390-448 (Maruzen Publishing Co., Ltd. 1977).

"Experimental Chemistry Course," First Edition, vol. 20, p. 471-489 (Maruzen Publishing Co., Ltd. 1956).

J. Brandrup et al., "Polymer Handbook," (U.S.), Third Edition, p. 209-277 (1989).

John Sheehan et al., "A Convenient Synthesis of Water-Soluble Carbodiimides," 26 (7) J. Org. Chem. 2525-2528 (Jul. 1961).

Office Action in Chinese Application No. 201180041700.X (dated Jan. 26, 2014).

U.S. Appl. No. 14/343,167, filed Mar. 6, 2014, Tanaka et al.

* cited by examiner

AZO COMPOUND, PIGMENT DISPERSANT CONTAINING THE AZO COMPOUND, PIGMENT COMPOSITION, PIGMENT DISPERSION, AND TONER

TECHNICAL FIELD

This invention relates to an azo compound, a pigment dispersant containing the azo compound, a pigment composition, a pigment dispersion (pigment disperse system), and a toner.

BACKGROUND ART

Pigments are versatile as colorants, and are widely used in the fields of coating materials, ink-jet inks, electrophotographic toners, color filters and so forth. When used in such fields, the pigments must finely be dispersed in mediums of various types in order to improve their coloring power and spectral characteristics such as transparency. However, such pigments having been made into fine particles commonly tend to cause the growth, transformation or the like of crystals because of their heat history and contact with solvents in the step of dispersion and subsequent steps for production to unwantedly cause problems such as a decrease in coloring power or transparency. Various pigment compositions and pigment dispersants for making up the compositions are proposed in order to remedy such problems. For example, a pigment composition is proposed in which an azo coloring matter different in type is added as a pigment dispersant to an azo pigment (see PTL 1). An example is also disclosed in which SOLSPERSE (registered trademark; available from Lubrizol Corporation) is used as a pigment dispersant (see PTL 2).

Meanwhile, as acetoacetanilide type disazo compounds, compounds various in chemical structure are proposed from old times as yellow or red colorants (see PTL 3).

CITATION LIST

Patent Literature

PTL 1: Japanese Patent Application Laid-open No. 2007-262382 (U.S. Pat. No. 7,384,472)
PTL 2: Japanese Patent Application Laid-open No. 2002-504586 (U.S. Pat. No. 6,099,631)
PTL 3: French Patent No. 2,106,450 (U.S. Pat. No. 4,003,886)
PTL 4: International Publication No. 2009-060886 Pamphlet
NPL 1: "Experimental Chemistry Course", Maruzen, First Edition, Vol. 19, pp. 176-188
NPL 2: Melvin S. Newman and one other "Journal of Organic Chemistry", (USA), American Chemical Society, 1961, Vol. 26, No. 7, pp. 2525-2528
NPL 3: Norman O. V. Sonntag "Chemical Reviews", (USA), American Chemical Society, 1953, Vol. 52, No. 2, pp. 237-416
NPL 4: "Experimental Chemistry Course", Maruzen, First Edition, Vol. 20, pp. 471-489
NPL 5: "Experimental Chemistry Course", Maruzen, Second Edition, Vol. 17-2, pp. 162-179
NPL 6: "New Experimental Chemistry Course", Maruzen, First Edition, Vol. 15, pp. 390-448
NPL 7: Datta E. Ponde and four others "Journal of Organic Chemistry", (USA), American Chemical Society, 1998, Vol. 63, No. 4, pp. 1058-1063
NPL 8: Kiran Kumar Solingapuran and two others "Journal of Organic Chemistry", (USA), American Chemical Society, 2007, Vol. 72, No. 25, pp. 9761-9764
NPL 9: "POLYMER HANDBOOK" Edited by J. Brandrup and E. H. Immergut, (U.S.A.), Third Edition, John Wiley & Sons, Inc., 1989, pp. 209-277

SUMMARY OF INVENTION

Technical Problem

Although various proposals have been made, it is still sought to more improve pigment dispersibility. For example, the dispersibility of pigments in binder resins in producing toners is a requirement that is important for toners to afford more improved color tones.

A subject the present invention aims to settle is to provide an azo compound which improves the pigment dispersibility and a pigment dispersant which contains such an azo compound. Another subject the present invention aims to settle is to provide a pigment composition having been improved in dispersibility of an azo pigment in virtue of such an azo compound. Still another subject the present invention aims to settle is to provide a pigment dispersion (pigment disperse system) in a non-water-soluble solvent of which the azo pigment has been improved in its state of dispersion. A further subject the present invention aims to settle is to provide a toner that affords a good color tone.

Solution to Problem

The above subjects are settled by the present invention described below. That is, the present invention provides an azo compound represented by the following formula (1).

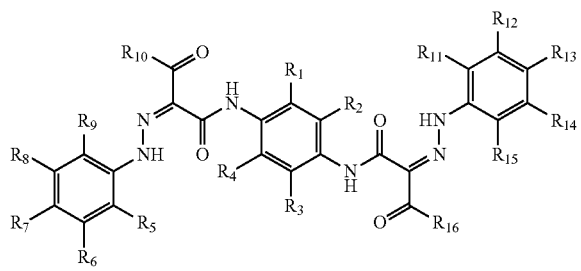

(1)

In the formula (1), $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $COOR_{17}$ group or the $CONR_{18}R_{19}$ group, where $R_{17}$ to $R_{19}$ each represent a hydrogen atom or an alkyl group having 1 to 3 carbon atom(s); $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group.

The present invention also provides a pigment dispersant containing the azo compound represented by the formula (1), a pigment composition, a pigment dispersion (pigment disperse system) and a toner.

Advantageous Effects of Invention

According to the present invention, a novel azo compound is provided. The azo compound represented by the formula (1) in the present invention has a high affinity for non-watersoluble solvents, in particular, non-polar solvents and also a high affinity for azo pigments, in particular, acetoacetanilide type pigments, and hence, by its use as a pigment dispersant, a pigment composition is provided which has been improved in dispersibility of an azo pigment. Also, by use of such a pigment composition, a pigment dispersion, in particular, a pigment dispersion of a styrene monomer is provided in which the azo pigment stand well dispersed in a non-water-soluble solvent. Further, by use of such a pigment composition, a toner is provided which affords a good color tone.

Further features of the present invention will become apparent from the following description of exemplary embodiments with reference to the attached drawings.

DESCRIPTION OF EMBODIMENTS

Figure 1:
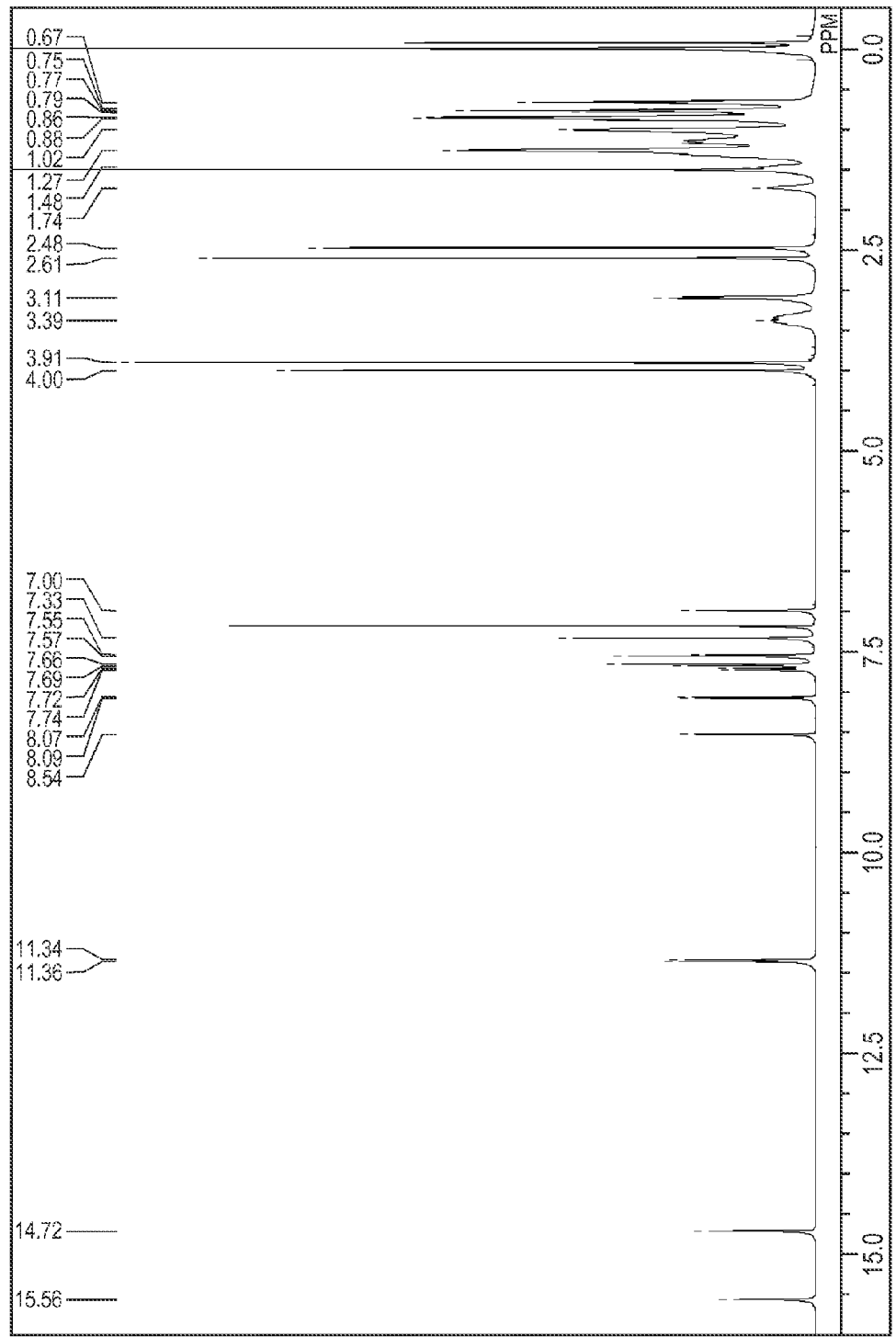
FIG. 1 is a graph showing a $^1$H-NMR spectrum of a compound (38) of the present invention.

The azo compound of the present invention is described below in greater detail.

As a result of extensive studies made in order to resolve problems the prior art has had, the present inventors have discovered that the azo compound represented by the above formula (1) has a high affinity for azo pigments and non-water-soluble solvents, and improves the dispersibility of the azo pigments in the non-water-soluble solvents. They have also discovered that an azo pigment composition having a good dispersibility is obtained by use of such an azo compound and further an azo pigment dispersion with an azo pigment standing well dispersed and a toner that affords a good color tone are provided by use of such a pigment composition. Thus, they have accomplished the present invention.

First, the azo compound according to the present invention, having a structure represented by the following formula (1), is described in detail.

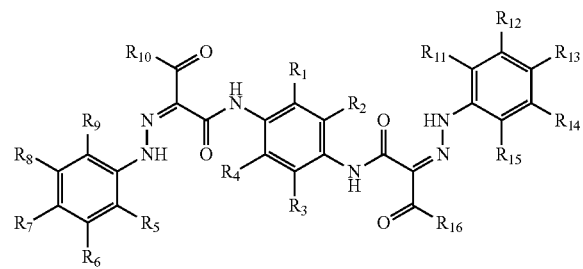

(1)

In the formula (1), $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $COOR_{17}$ group or the $CONR_{18}R_{19}$ group, where $R_{17}$ to $R_{19}$ each represent a hydrogen atom or an alkyl group having 1 to 3 carbon atom(s); $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group.

The azo compound represented by the formula (1) is constituted of the $L_1R_{20}$ group or $L_2R_{21}R_{22}$ group that contributes to an affinity between i) a coloring matter base skeleton contributing to the affinity for the azo pigment and ii) the non-water-soluble solvent.

The coloring matter base skeleton contributing to the affinity for the pigment is described first.

The halogen atom that may be represented by $R_1$ to $R_4$ each in the formula (1) is a fluorine atom, a chlorine atom, a bromine atom or an iodine atom.

$R_1$ to $R_4$ in the formula (1) may each arbitrarily be selected from a halogen atom and a hydrogen atom. It, however, may each preferably be a hydrogen atom in view of the affinity of the azo compound represented by the formula (1) with the pigment.

$R_5$ to $R_9$ in the formula (1) may each be so selected from a hydrogen atom, a $COOR_{17}$ group and a $CONR_{18}R_{19}$ group that at least one of them may be the $COOR_{17}$ group or the $CONR_{18}R_{19}$ group. It, however, is preferable in view of pigment dispersibility that $R_5$ and $R_8$ are all $COOR_{17}$ groups and $R_6$, $R_7$ and $R_9$ are all hydrogen atoms.

The alkyl group that may be represented by $R_{17}$ to $R_{19}$ each of the $COOR_{17}$ group and $CONR_{18}R_{19}$ group in the formula (1) is a methyl group, an ethyl group or a n-propyl group.

$R_{17}$ to $R_{19}$ of the same in the formula (1) may each arbitrarily be selected from an alkyl group having 1 to 3 carbon atom(s) and a hydrogen atom. In view of the affinity of the azo compound represented by the formula (1) with the pigment, however, it is preferable that $R_{17}$ is a methyl group where any of $R_5$ to $R_9$ in the formula (1) is the $COOR_{17}$ group, and also it is preferable that $R_{18}$ is a methyl group and $R_{19}$ is a hydrogen atom or a methyl group where any of $R_5$ to $R_9$ in the formula (1) is the $CONR_{18}R_{19}$ group.

The alkyl group that may be represented by $R_{10}$ in the formula (1) may at least be an alkyl group having 1 to 6 carbon atom(s), and may include, e.g., a methyl group, an ethyl group, a propyl group, a butyl group, a pentyl group and a hexyl group. These may be of any structure of straight-chain, branched and cyclic ones.

$R_{10}$ in the formula (1) may further be substituted with a substituent as long as the affinity of the azo compound represented by the formula (1) with the pigment is not greatly inhibited. The substituent in such a case may include a halogen atom, a nitro group, an amino group, a hydroxyl group and a cyano group.

$R_{10}$ in the formula (1) may arbitrarily be selected from an alkyl group having 1 to 6 carbon atom(s) and a phenyl group. It, however, may preferably be a methyl group in view of the affinity of the azo compound represented by the formula (1) with the pigment.

The alkyl group that may be represented by $R_{16}$ in the formula (1) may preferably be one having 1 to 6 carbon atom(s), and may include, e.g., a methyl group, an ethyl group, a propyl group, a butyl group, a pentyl group, a hexyl group. These alkyl groups may be of any structure of straight-chain, branched and cyclic ones.

$R_{16}$ in the formula (1) may further be substituted with a substituent as long as the affinity of the azo compound represented by the formula (1) with the pigment is not greatly inhibited. The substituent in such a case may include a halogen atom, a nitro group, an amino group, a hydroxyl group and a cyano group. $R_{16}$ in the formula (1) may arbitrarily be selected from an alkyl group having 1 to 6 carbon atom(s) and a phenyl group. It, however, may preferably be a methyl group in view of readiness for synthesis.

The $L_1R_{20}$ group and $L_2R_{21}R_{22}$ group that contribute to an affinity for the non-water-soluble solvent are described next.

At least one of $R_{11}$ to $R_{15}$ in the formula (1) represents the $L_1R_{20}$ group or the $L_2R_{21}R_{22}$ group, and remainder represents a hydrogen atom.

$L_1$ of the $L_1R_{20}$ group in the formula (1) is a divalent linking group, and represents, but is not particularly limited to, e.g.:

a carbonyl group

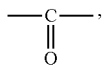

a secondary amino group

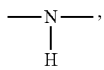

an ether group

a thioether group

a carboxylate group

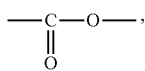

a carboxylic acid secondary amide group

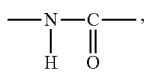

a sulfonate group

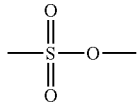

or a sulfonic acid secondary amide group

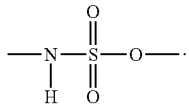

$L_1$ may preferably be a carboxylate group, a carboxylic acid secondary amide group, a sulfonate group or a sulfonic acid secondary amide group in view of readiness for synthesis, and much preferably be a carboxylate group or a carboxylic acid secondary amide group.

$L_2$ of the $L_2R_{21}R_{22}$ group in the formula (1) is a trivalent linking group, and represents, but is not particularly limited to, e.g.:

a tertiary amino group

a carboxylic acid tertiary amide group

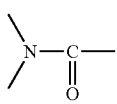

or a sulfonic acid tertiary amide group

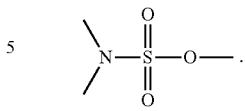

$L_2$ may preferably be a carboxylic acid tertiary amide group or a sulfonic acid tertiary amide group in view of readiness for synthesis, and much preferably be a carboxylic acid tertiary amide group.

The alkyl group that may be represented by $R_{20}$ to $R_{22}$ each in the formula (1) is not particularly limitative as long it is one having 8 or more carbon atoms (preferably 8 or more to 30 or less carbon atoms), and may include, e.g., an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a tricosyl group, a tetracosyl group, a pentacosyl group, a hexacosyl group, a heptacosyl group, an octacosyl group, a nonacosyl group and a triacontyl group. These alkyl groups may be of any structure of straight-chain, branched and cyclic ones.

The alkenyl group that may be represented by $R_{20}$ to $R_{22}$ each of the $L_1R_{20}$ group and $L_2R_{21}R_{22}$ group in the formula (1) is not particularly limitative as long it is one having 8 or more carbon atoms (preferably 8 or more to 30 or less carbon atoms), and may include, e.g., an octenyl group, a nonenyl group, a decenyl group, a undecenyl group, a dodecenyl group, a tridecenyl group, a tetradecenyl group, a pentadecenyl group, a hexadecenyl group, a heptadecenyl group, an octadecenyl group, a nonadecenyl group, an eicosenyl group, a heneicosenyl group, a docosenyl group, a tricosenyl group, a tetracosenyl group, a pentacosenyl group, a hexacosenyl group, a heptacosenyl group, an octacosenyl group, a nonacosenyl group and a triacontenyl group. These alkenyl groups may be of any structure of straight-chain, branched and cyclic ones. Also, these may each have the double bond at any position, and may have at least one double bond.

$R_{20}$ to $R_{22}$ of the same in the formula (1) may each further be substituted with a substituent. The substituent in such a case may include a halogen atom, a nitro group, an amino group, a hydroxyl group and a cyano group.

$R_{20}$ to $R_{22}$ of the same in the formula (1) may preferably be those each having 30 or less carbon atoms, in view of the affinity of the azo compound represented by the formula (1) with the pigment. When the azo compound represented by the formula (1) is used as a pigment dispersant, the $R_{20}$ to $R_{22}$ may also preferably be those in which the total sum of carbon atoms of all $R_{20}$ to $R_{22}$ in the formula (1) (where a plurality of $R_{20}$ to $R_{22}$ are present in the formula (1), the total sum of carbon atoms of all of them) is 10 or more, in view of pigment dispersibility.

As the azo compound represented by the formula (1), tautomers having structures of the following formulas (3) and (4) or the like are present, as shown by the following scheme. About these tautomers as well, they fall under the right of the present invention.

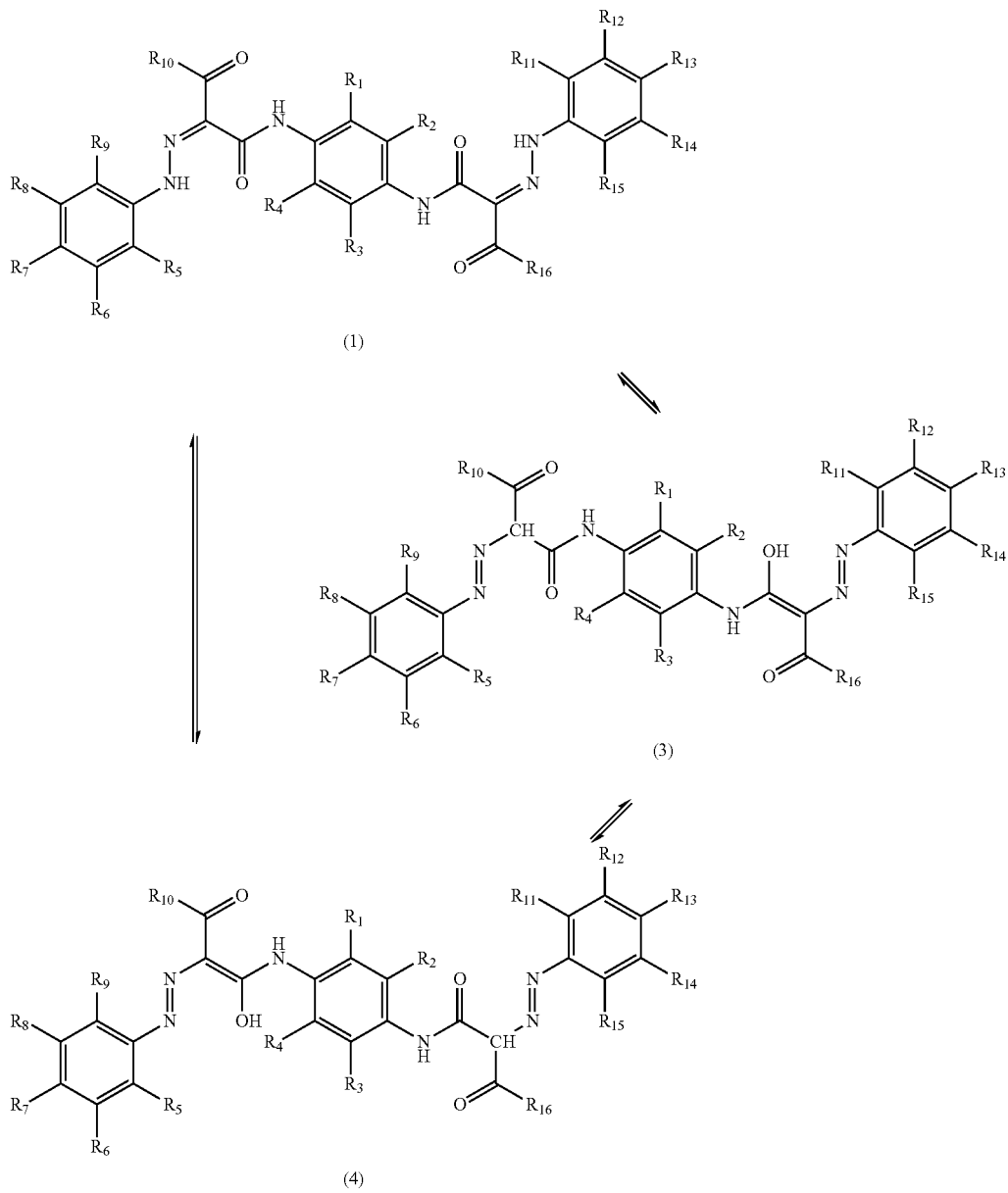
[$R_1$ to $R_{16}$ in the formulas (3) and (4) are as defined for $R_1$ to $R_{16}$, respectively, in the formula (1).]
The azo compound represented by the formula (1) in the present invention may be produced by a known synthesis method. An example of a synthesis scheme is shown below.
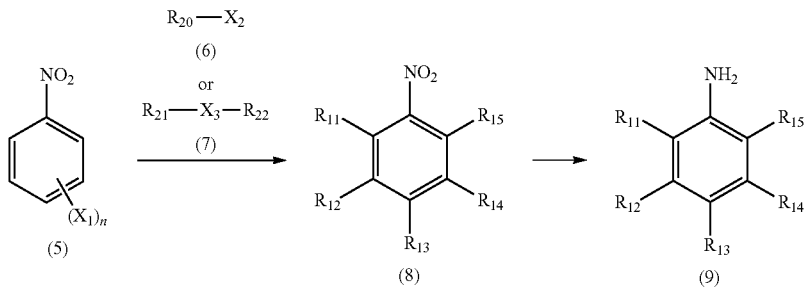

-continued

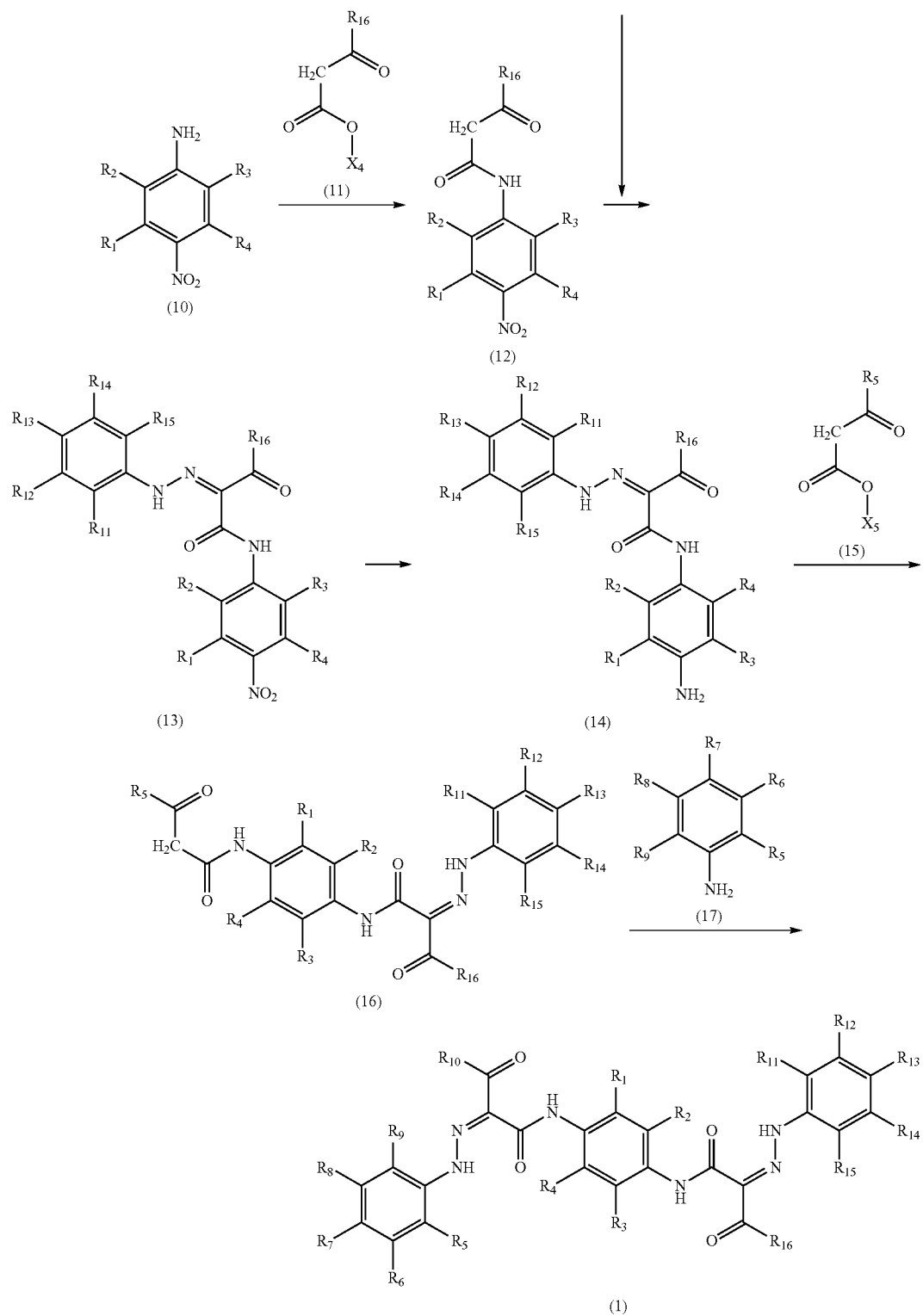

[$R_1$ to $R_{16}$ and $R_{20}$ to $R_{22}$ in the formulas (5) to (17) are as defined for $R_1$ to $R_{16}$ and $R_{20}$ to $R_{22}$, respectively, in the formula (1); $X_1$ to $X_3$ are each a substituent which reacts to form the linking group $L_1$ or $L_2$ in the formula (1); $X_4$ and $X_5$ are each a leaving group; and n is 1 to 5.]

In the synthesis scheme exemplified above, the azo compound represented by the formula (1) of the present invention is obtained through a step 1 where a raw material (5) and a raw material (6) or (7) are used to synthesize an intermediate (8), a step 2 where the nitro group of the intermediate (8) is reduced to synthesize an intermediate (9), a step 3 where a raw material (10) and a raw material (11) are used to make the former into an amide to synthesize an intermediate (12) that is an acetanilide analogue, a step 4 where the intermediate (9) and the intermediate (12) are coupled with each other to synthesize an intermediate (13) that is an azo compound, a step 5 where the nitro group of the intermediate (13) is reduced to synthesize an intermediate (14), a step 6 where the intermediate (14) and a raw material (15) are used to make the former into an amide to synthesize an intermediate (16) and a step 7 where the intermediate (6) and a raw material (17) are coupled.

The step 1 is described first. In the step 1, a known method may be used. Stated specifically, the azo compound represented by the formula (1) the linking group $L_1$ of which comes into an ether group can be synthesized by using an intermediate in which $X_1$ in the formula (5) is a hydroxyl group and n is 1 and a raw material in which $X_2$ in the formula (6) is a halogen atom as exemplified by a chlorine atom, a bromine atom or an iodine atom (see, e.g., NPL 1).

The azo compound represented by the formula (1) the linking group $L_2$ of which comes into a carboxylic acid tertiary amide group can be synthesized by using an intermediate in which $X_1$ in the formula (5) is a carboxylic acid group and n is 1 and a raw material in which $X_3$ in the formula (7) is a secondary amino group. Stated specifically, what is available is a method making use of a dehydration condensation agent as exemplified by 1-ethyl-3-(3-dimethylaminopropyl) carbodimide hydrochloride or the like (see, e.g., NPL 2), or the Schotten-Baumann method (see, e.g., NPL 3).

The azo compound represented by the formula (1) the linking group $L_1$ of which comes into a secondary amino group or the linking group $L_2$ of which comes into a tertiary amino group can be synthesized by using the raw material (5) the $X_1$ of which is a primary amino group and the raw material (5) the $X_2$ of which is a halogen atom as exemplified by a chlorine atom, a bromine atom or an iodine atom (see, e.g., NPL 4).

The raw materials (5) to (7) appear on the market in many kinds, and are readily available. These may also be synthesized with ease by any known method.

The present step may be carried out without any solvent. It, however, may preferably be carried out in the presence of a solvent in order to prevent the reaction from proceeding abruptly. As the solvent, there are no particular limitations thereon as long as it is what does not inhibit the reaction. It may include, e.g., ethers such as diethyl ether, tetrahydrofuran and dioxane; hydrocarbons such as benzene, toluene, xylene, hexane and heptane; halogen-containing hydrocarbons such as dichloromethane, dichloroethane and chloroform; amides such as N,N-dimethylformamide and N,N-dimethylimidasolidinone; and nitriles such as acetonitrile and propionitrile. Any of these solvents may also be used in the form of a mixture of two or more types in accordance with the solubility of substrates, and the mixing ratio in using them in the form of a mixture may be set as desired. The solvent may be used in an amount set as desired, which may preferably be in an amount ranging from 1.0 to 20.0 times by mass that of the compound represented by the formula (5), in view of reaction rate.

The present step is usually carried out in a temperature range of from 0° C. to 250° C., and is usually completed within 24 hours.

The step 2 is described next. In the step 2, a known method may be used. Stated specifically, it may include, e.g., reduction reaction making use of a metal compound, iron, tin or the like and an acid, hydrochloric acid, acetic acid or the like (see, e.g., NPL 5) and a catalytic hydrogenation process (see, e.g., NPL 6, and PTL 4).

The present step may be carried out without any solvent. It, however, may preferably be carried out in the presence of a solvent in order to prevent the reaction from proceeding abruptly. As the solvent, there are no particular limitations thereon as long as it is what does not inhibit the reaction. It may include, e.g., alcohols such as methanol, ethanol and propanol; esters such as methyl acetate, ethyl acetate and propyl acetate; ethers such as diethyl ether, tetrahydrofuran and dioxane; hydrocarbons such as benzene, toluene, xylene, hexane and heptane; halogen-containing hydrocarbons such as dichloromethane, dichloroethane and chloroform; amides such as N,N-dimethylformamide and N,N-dimethylimidasolidinone; nitriles such as acetonitrile and propionitrile; acids such as formic acid, acetic acid and propionic acid; and water. Any of these solvents may also be used in the form of a mixture of two or more types in accordance with the solubility of substrates, and the mixing ratio in using them in the form of a mixture may be set as desired. The solvent may be used in an amount set as desired, which may preferably be in an amount ranging from 1.0 to 20.0 times by mass that of the compound represented by the formula (8), in view of reaction rate.

The present step is usually carried out in a temperature range of from 0° C. to 250° C., and is usually completed within 24 hours.

The step 3 is described next. In the step 3, a known method may be used (see, e.g., NPL 7). Also, where $R_{16}$ in the formula (11) is a methyl group, the compound may be synthesized by a method making use of diketone in place of the raw material (11) (see, e.g., NPL 8).

The raw materials (10) to (11) appear on the market in many kinds, and are readily available. These may also be synthesized with ease by any known method.

The present step may be carried out without any solvent. It, however, may preferably be carried out in the presence of a solvent in order to prevent the reaction from proceeding abruptly. As the solvent, there are no particular limitations thereon as long as it is what does not inhibit the reaction. It may include, e.g., alcohols such as methanol, ethanol and propanol; esters such as methyl acetate, ethyl acetate and propyl acetate; ethers such as diethyl ether, tetrahydrofuran and dioxane; hydrocarbons such as benzene, toluene, xylene, hexane and heptane; halogen-containing hydrocarbons such as dichloromethane, dichloroethane and chloroform; amides such as N,N-dimethylformamide and N,N-dimethylimidasolidinone; nitriles such as acetonitrile and propionitrile; acids such as formic acid, acetic acid and propionic acid; and water. Any of these solvents may also be used in the form of a mixture of two or more types in accordance with the solubility of substrates, and the mixing ratio in using them in the form of a mixture may be set as desired. The solvent may be used in an amount set as desired, which may preferably be in an amount ranging from 1.0 to 20.0 times by mass that of the compound represented by the formula (10), in view of reaction rate.

The present step is usually carried out in a temperature range of from 0° C. to 250° C., and is usually completed within 24 hours.

The step 4 is described next. In the step 4, a known method may be used. Stated specifically, it may include, e.g., a method shown below. First, in a methanol solvent, the intermediate (9) is allowed to react with a diazo-forming agent such as sodium nitrite or nitrosyl hydrogensulfate in the presence of an inorganic acid such as hydrochloric acid or sulfuric acid to synthesize a corresponding diazonium salt. Further, this diazonium salt is coupled with the intermediate (12) to synthesize the intermediate (13).

The present step may be carried out without any solvent. It, however, may preferably be carried out in the presence of a solvent in order to prevent the reaction from proceeding abruptly. As the solvent, there are no particular limitations thereon as long as it is what does not inhibit the reaction. It may include, e.g., alcohols such as methanol, ethanol and propanol; esters such as methyl acetate, ethyl acetate and propyl acetate; ethers such as diethyl ether, tetrahydrofuran and dioxane; hydrocarbons such as benzene, toluene, xylene, hexane and heptane; halogen-containing hydrocarbons such as dichloromethane, dichloroethane and chloroform; amides such as N,N-dimethylformamide and N,N-dimethylimidaso-lidinone; nitriles such as acetonitrile and propionitrile; acids such as formic acid, acetic acid and propionic acid; and water. Any of these solvents may also be used in the form of a mixture of two or more types in accordance with the solubility of substrates, and the mixing ratio in using them in the form of a mixture may be set as desired. The solvent may be used in an amount set as desired, which may preferably be in an amount ranging from 1.0 to 20.0 times by mass that of the compound represented by the formula (9), in view of reaction rate.

The present step is usually carried out in a temperature range of from −50° C. to 100° C., and is completed within 24 hours.

The step 5 is described next. In the step 5, the same procedure as that in the step 2 is used to synthesize the intermediate (14).

The step 6 is described next. In the step 6, the same procedure as that in the step 3 is used to synthesize the intermediate (16).

The step 7 is described next. In the step 7, the same procedure as that in the step 4 is used to synthesize the azo compound represented by the formula (1).

The raw material (17) appears on the market in many kinds, and is readily available. These may also be synthesized with ease by any known method.

The compounds represented by the formulas (1), (8), (9), (12), (13), (14) and (16) which have been obtained in the respective steps may make use of any conventional methods for isolation and purification of organic compounds. The methods for isolation and purification are, e.g., recrystallization or reprecipitation making use of an organic solvent and column chromatography making use of silica gel or the like. Any of these methods may be used alone or in combination of two or more types to effect purification to obtain the compounds in higher purities.

The compounds represented by the formulas (1), (8), (9), (12), (13), (14) and (16) which have been obtained in the respective steps have been identified and quantitatively determined with nuclear magnetic resonance spectroscopy ($^1$H-NMR) (ECA-400, manufactured by JEOL Ltd.), mass spectrometry (LC/MSD TOF, manufactured by Agilent Technologies Inc.) and HPLC analysis (LC-20A, manufactured by Shimadzu Corporation).

The azo compound represented by the formula (1) can be produced by the production process described above. In the following Tables 1 to 6, azo compounds (18) to (51) are shown as specific examples of the present invention, to which, however, examples are by no means limited. "Ph" in the tables represents an unsubstituted phenyl group, and "*" represents a linking site of a substituent.

TABLE 1

Azo Compounds of The Invention

| Compound | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 18 | H  | H | H | H | COOCH$_3$ | H | H | COOCH$_3$ | H | C$_6$H$_{13}$ | H |
| 19 | Cl | H | H | H | COOCH$_3$ | H | H | COOCH$_3$ | H | CH$_3$ | H |
| 20 | H  | H | H | H | COOCH$_3$ | H | H | COOCH$_3$ | H | CH$_3$ | H |
| 21 | H  | H | H | H | COOCH$_3$ | H | H | COOCH$_3$ | H | CH$_3$ | H |
| 22 | H  | H | H | H | COOCH$_3$ | H | H | COOCH$_3$ | H | CH$_3$ | H |
| 23 | H  | H | H | H | COOCH$_3$ | H | H | COOCH$_3$ | H | CH$_3$ | H |
| 24 | H  | H | H | H | COOCH$_3$ | H | H | COOCH$_3$ | H | CH$_3$ | H |
| 25 | H  | H | H | H | COOCH$_3$ | H | H | COOCH$_3$ | H | CH$_3$ | H |

Azo Compounds of The Invention

| Compound | $R_{12}$ | $R_{13}$ | $R_{14}$ | $R_{15}$ | $R_{16}$ |
|---|---|---|---|---|---|
| 18 | CH(C$_2$H$_5$)(C$_4$H$_9$)—CH$_2$—N(*)(C=O)—CH$_2$—CH(C$_4$H$_9$)(C$_2$H$_5$) | H | CH(C$_2$H$_5$)(C$_4$H$_9$)—CH$_2$—N(*)(C=O)—CH$_2$—CH(C$_4$H$_9$)(C$_2$H$_5$) | H | Ph |
| 19 | CH(C$_2$H$_5$)(C$_4$H$_9$)—CH$_2$—N(*)(C=O)—CH$_2$—CH(C$_4$H$_9$)(C$_2$H$_5$) | H | CH(C$_2$H$_5$)(C$_4$H$_9$)—CH$_2$—N(*)(C=O)—CH$_2$—CH(C$_4$H$_9$)(C$_2$H$_5$) | H | CH$_3$ |

TABLE 1-continued

| # | Col A | Col B | Col C | Col D | Col E |
|---|-------|-------|-------|-------|-------|
| 20 | H | *—NH—C(=O)—C7H14—CH=CH—C8H17 | H | H | CH3 |
| 21 | *—C(=O)—NH—CH2—CH(C2H)(C4H9) | *—C(=O)—NH—CH2—CH(C2H5)(C4H9) | | | CH3 |
| 22 | H | *—S(=O)2—O—C8H16—CH=CH—C8H17 | H | H | CH3 |
| 23 | H | *—S(=O)2—NH—C8H16—CH=CH—C8H17 | H | H | CH3 |
| 24 | *—C(=O)—O—CH2—CH(C2H)(C4H9) | *—C(=O)—O—CH2—CH(C2H5)(C4H9) | | | CH3 |
| 25 | H | *—NH—CH2—CH(C2H5)(C4H9) | H | H | CH3 |

TABLE 2

Azo Compounds of The Invention

| Compound | R1 | R2 | R3 | R4 | R5 | R6 | R7 | R8 | R9 | R10 | R11 |
|----------|----|----|----|----|----|----|----|----|----|----|----|
| 26 | H | H | H | H | COOH | H | H | COOH | H | CH3 | H |
| 27 | H | H | H | H | COOC2H5 | H | H | COOC2H5 | H | CH3 | H |
| 28 | H | H | H | H | COOC3H7 | H | H | COOC3H7 | H | CH3 | H |
| 29 | H | H | H | H | CONH2 | H | H | CONH2 | H | CH3 | H |
| 30 | H | H | H | H | CONHCH3 | H | H | CONHCH3 | H | CH3 | H |
| 31 | H | H | H | H | CONHC2H5 | H | H | CONHC2H5 | H | CH3 | H |

Azo Compounds of The Invention

| Compound | R12 | R13 | R14 | R15 | R16 |
|----------|-----|-----|-----|-----|-----|
| 26 | *—C(=O)—N(CH2CH(C2H5)(C4H9))(CH2CH(C4H9)(C2H5)) | H | *—C(=O)—N(CH2CH(C2H5)(C4H9))(CH2CH(C4H9)(C2H5)) | H | CH3 |
| 27 | *—C(=O)—N(CH2CH(C2H5)(C4H9))(CH2CH(C4H9)(C2H5)) | H | *—C(=O)—N(CH2CH(C2H5)(C4H9))(CH2CH(C4H9)(C2H5)) | H | CH3 |

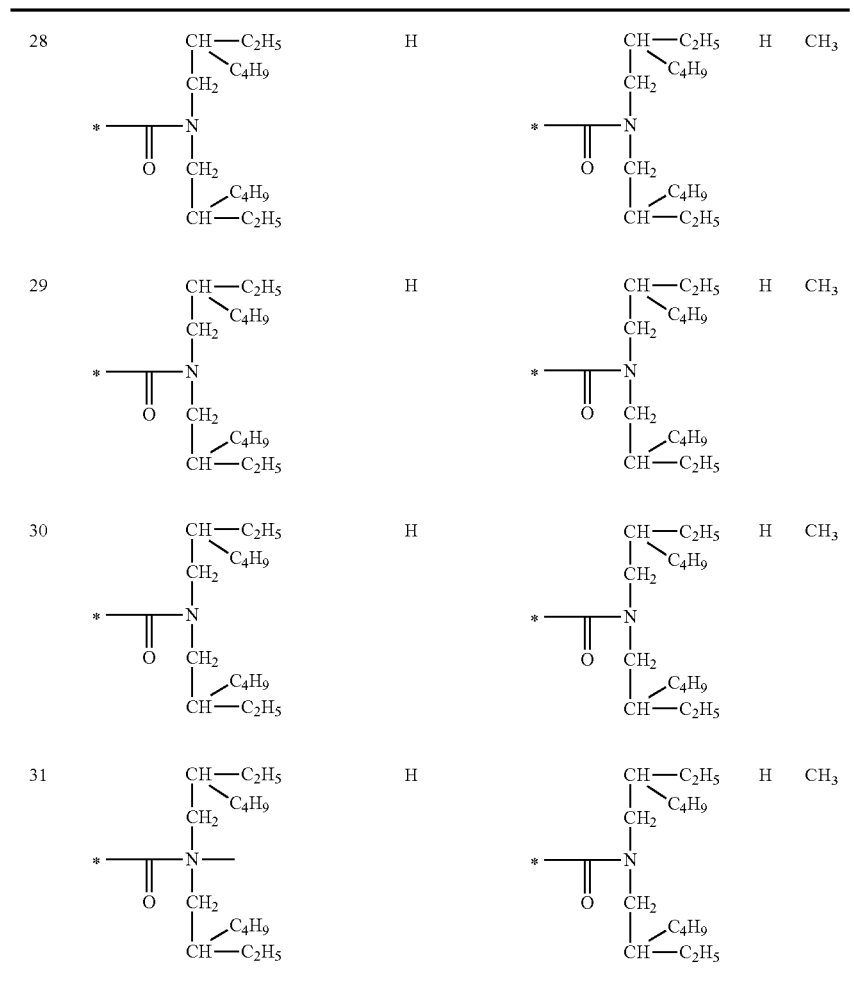
TABLE 3
Azo Compounds of The Invention
| Compound | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 32 | H | H | H | H | $CONHC_3H_7$ | H | H | $CONHC_3H_7$ | H | $CH_3$ | H |
| 33 | H | H | H | H | $CON(CH_3)_2$ | H | H | $CON(CH_3)_2$ | H | $CH_3$ | H |
| 34 | H | H | H | H | $COOCH_3$ | H | H | H | H | $CH_3$ | H |
| 35 | H | H | H | H | H | $COOCH_3$ | H | H | H | $CH_3$ | H |
| 36 | H | H | H | H | H | H | $COOCH_3$ | H | H | $CH_3$ | H |
| 37 | H | H | H | H | H | $COOCH_3$ | H | $COOCH_3$ | H | $CH_3$ | H |
Azo Compounds of The Invention TABLE 3-continued

| # | (left group) | R | (right group) | R | R |
|---|---|---|---|---|---|
| 33 | *—C(O)—N(CH₂CH(C₄H₉)(C₂H₅))(CH₂CH(C₄H₉)(C₂H₅)) | H | *—C(O)—N(CH₂CH(C₄H₉)(C₂H₅))(CH₂CH(C₄H₉)(C₂H₅)) | H | CH₃ |
| 34 | *—C(O)—N(CH₂CH(C₄H₉)(C₂H₅))(CH₂CH(C₄H₉)(C₂H₅)) | H | *—C(O)—N(CH₂CH(C₄H₉)(C₂H₅))(CH₂CH(C₄H₉)(C₂H₅)) | H | CH₃ |
| 35 | *—C(O)—N(CH₂CH(C₄H₉)(C₂H₅))(CH₂CH(C₄H₉)(C₂H₅)) | H | *—C(O)—N(CH₂CH(C₄H₉)(C₂H₅))(CH₂CH(C₄H₉)(C₂H₅)) | H | CH₃ |
| 36 | *—C(O)—N(CH₂CH(C₄H₉)(C₂H₅))(CH₂CH(C₄H₉)(C₂H₅)) | H | *—C(O)—N(CH₂CH(C₄H₉)(C₂H₅))(CH₂CH(C₄H₉)(C₂H₅)) | H | CH₃ |
| 37 | *—C(O)—N(CH₂CH(C₄H₉)(C₂H₅))(CH₂CH(C₄H₉)(C₂H₅)) | H | *—C(O)—N(CH₂CH(C₄H₉)(C₂H₅))(CH₂CH(C₄H₉)(C₂H₅)) | H | CH₃ |

TABLE 4

Azo Compounds of The Invention

| Compound | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 38 | H | H | H | H | COOCH₃ | H | H | COOCH₃ | H | CH₃ | H |
| 39 | H | H | H | H | COOCH₃ | H | H | COOCH₃ | H | CH₃ | H |
| 40 | H | H | H | H | COOCH₃ | H | H | COOCH₃ | H | CH₃ | H |
| 41 | H | H | H | H | COOCH₃ | H | H | COOCH₃ | H | CH₃ | H |
| 42 | H | H | H | H | COOCH₃ | H | H | COOCH₃ | H | CH₃ | H |
| 43 | H | H | H | H | COOCH₃ | H | H | COOCH₃ | H | CH₃ | H |
| 44 | H | H | H | H | COOCH₃ | H | H | COOCH₃ | H | CH₃ | H |

TABLE 4-continued

Azo Compounds of The Invention

| Compound | $R_{12}$ | $R_{13}$ | $R_{14}$ | $R_{15}$ | $R_{16}$ |
|---|---|---|---|---|---|
| 38 | *−C(=O)−N(CH(C₂H₅)CH₂C₄H₉)(CH₂CH(C₄H₉)C₂H₅) | H | *−C(=O)−N(CH(C₂H₅)CH₂C₄H₉)(CH₂CH(C₄H₉)C₂H₅) | H | $CH_3$ |
| 39 | *−C(=O)−O−CH₂−CH(C₂H₅)(C₄H₉) | *−C(=O)−O−CH₂−CH(C₂H₅)(C₄H₉) | H | H | $CH_3$ |
| 40 | H | *−NH−C(=O)−(adamantyl) | H | H | $CH_3$ |
| 41 | H | *−C(=O)−O−CH₂−CH(C₂H₅)(C₄H₉) | H | H | $CH_3$ |
| 42 | H | *−C(=O)−O−C₄H₈−CH=C(CH₃)₂ | H | H | $CH_3$ |
| 43 | H | *−NH−C(=O)−CH(C₂H₄CH(CH₃)CH₂C(CH₃)₂CH₃)(CH(CH₃)CH₂C(CH₃)₂CH₃) | H | H | $CH_3$ |
| 44 | H | *−NH−C(=O)−C₇H₁₄−CH=CH−CH₂−CH=CH−C₅H₁₁ | H | H | $CH_3$ |

TABLE 5

Azo Compounds of The Invention

| Compound | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 45 | H | H | H | H | $COOCH_3$ | H | H | $COOCH_3$ | H | $CH_3$ | H |
| 46 | H | H | H | H | $COOCH_3$ | H | H | $COOCH_3$ | H | $CH_3$ | H |
| 47 | H | H | H | H | $COOCH_3$ | H | H | $COOCH_3$ | H | $CH_3$ | H |
| 48 | H | H | H | H | $COOCH_3$ | H | H | $COOCH_3$ | H | $CH_3$ | H |

TABLE 5-continued
Azo Compounds of The Invention
| Compound | $R_{12}$ | $R_{13}$ | $R_{14}$ | $R_{15}$ | $R_{16}$ |
|---|---|---|---|---|---|
| 45 | H | 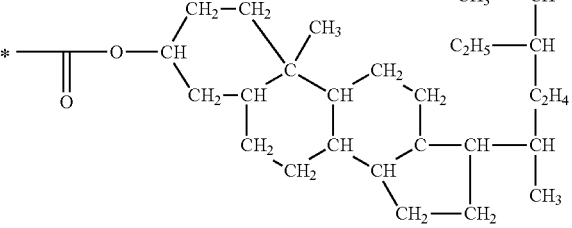 | H | H | $CH_3$ |
| 46 | H | 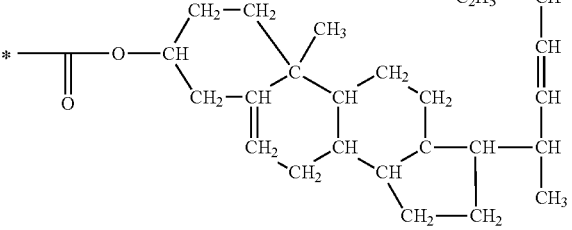 | H | H | $CH_3$ |
| 47 | H | 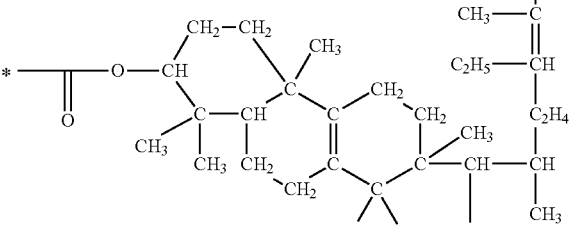 | H | H | $CH_3$ |
| 48 | H | 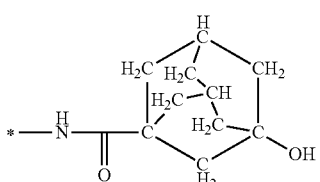 | H | H | $CH_3$ |

TABLE 6

Azo Compounds of The Invention

| Compound | R₁ | R₂ | R₃ | R₄ | R₅ | R₆ | R₇ | R₈ | R₉ | R₁₀ | R₁₁ |
|---|---|---|---|---|---|---|---|---|---|---|---|
| 49 | H | H | H | H | COOCH₃ | H | H | COOCH₃ | H | CH₃ | *—C(=O)—N(CH₂CH(C₂H₅)C₄H₉)₂ |
| 50 | H | H | H | H | COOCH₃ | H | H | COOCH₃ | H | CH₃ | H |
| 51 | H | H | H | H | COOCH₃ | H | H | COOCH₃ | H | Ph | H |

Azo Compounds of The Invention

| Compound | R₁₂ | R₁₃ | R₁₄ | R₁₅ | R₁₆ |
|---|---|---|---|---|---|
| 49 | H | H | *—C(=O)—N(CH₂CH(C₂H₅)C₄H₉)₂ | H | CF₃ |
| 50 | *—C(=O)—O—C₈H₁₆—CH=CH—C₈H₁₇ | *—C(=O)—O—C₈H₁₆—CH=CH—C₈H₁₇ | H | H | CH₃ |
| 51 | *—C(=O)—N(CH₂CH(C₂H₅)C₄H₉)₂ | H | *—C(=O)—N(CH₂CH(C₂H₅)C₄H₉)₂ | H | C₄H₉ |

The pigment dispersant and pigment composition of the present invention are described next. The azo compound of the present invention has a high affinity for azo pigments, in particular, acetoacetanilide type pigments, and also has a high affinity for non-water-soluble solvents as well, and hence as a pigment dispersant it may be used alone or in combination of two or more types.

The pigment composition of the present invention is used in coating materials, inks, toners and resin molded products, and is characterized by containing an azo pigment and the azo compound represented by the formula (1) as the pigment dispersant.

The pigment usable in the present invention may include monoazo pigments, disazo pigments and polyazo pigments. Of these, acetoacetanilide type pigments as typified by C.I. Pigment Yellow 74, C.I. Pigment Yellow 93, C.I. Pigment Yellow 128, C.I. Pigment Yellow 155 and C.I. Pigment Yellow 180 are preferable because they have stronger affinity with the pigment dispersant of the present invention. In particular, C.I. Pigment Yellow 155, which is represented by the following formula (2), is much preferable because it can highly effectively be dispersed by the azo compound represented by the formula (1). Any of these pigments may be used alone or in the form of a mixture of two or more types.

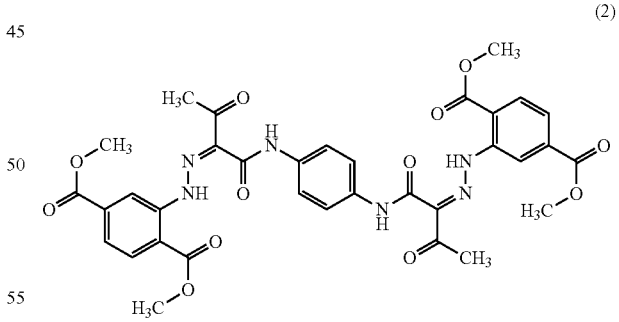

(2)

As the pigment usable in the present invention, even a pigment other than such a yellow pigment as the above may also preferably be used as long as it is a pigment having an affinity for the pigment dispersant of the present invention, and is not limitative.

Such a pigment preferably also usable in the present invention may include, e.g., azo pigments such as C.I. Pigment Orange 1, 5, 13, 15, 16, 34, 36, 38, 62, 64, 67, 72, 74; C.I. Pigment Red 2, 3, 4, 5, 12, 16, 17, 23, 31, 32, 41, 47, 48, 48:1, 48:2, 53:1, 57:1, 112, 144, 146, 166, 170, 176, 185, 187, 208, 210, 220, 221, 238, 242, 245, 253, 258, 266, 269; C.I. Pigment Violet 13, 25, 32, 50; C.I. Pigment Blue 25, 26; and C.I. Pigment Brown 23, 25, 41.

These may be crude pigments or may be pigment compositions prepared as such, as long as they are those which may not greatly inhibit the effect of the pigment dispersant of the present invention.

The pigment and pigment dispersant in the pigment composition of the present invention may preferably be in a mass compositional ratio (mass of pigment:mass of pigment dispersant) ranging from 100:0.1 to 100:20, and much preferably ranging from 100:1 to 100:10. The controlling of mass compositional ratio of the pigment to the pigment dispersant in this way enables the pigment dispersant to contribute appropriately to the dispersibility of the pigment to achieve much better color tone.

The pigment composition of the present invention may be produced by a wet process or a dry process. Taking account of the fact that the azo compound of the present invention has a high affinity for non-water-soluble solvents, it may preferably be produced by the wet process, which can simply produce a uniform pigment composition. Stated specifically, it may be obtained in the following way, for example. The pigment dispersant and optionally a resin are dissolved into a dispersion medium, and a pigment powder is slowly added thereto with stirring to well adapt it to the dispersion medium. Further, a mechanical shear force is applied by using a dispersion machine such as a kneader, a roll mill, a ball mill, a paint shaker, a dissolver, an attritor, a sand mill or a high-speed mill, whereby the pigment dispersant can be adsorbed to particle surfaces of the pigment and the pigment can stably be dispersed in the form of uniform fine particles.

As the dispersion medium usable in the pigment composition of the present invention, it may be selected according to the use purposes of the pigment composition, and there are no particular limitations thereon. It, however, is preferable for the dispersion medium to be a non-water-soluble solvent. The non-water-soluble solvent may specifically include, e.g., esters such as methyl acetate, ethyl acetate and propyl acetate; hydrocarbons such as hexane, octane, petroleum ether, cyclohexane, benzene, toluene and xylene; and halogen-containing hydrocarbons such as carbon tetrachloride, trichloroethylene and tetrabromoethane.

The dispersion medium usable in the pigment composition of the present invention may also be a polymerizable monomer. Stated specifically, it may include styrene, α-methylstyrene, α-ethylstyrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, ethylene, propylene, butylene, isobutylene, vinyl chloride, vinylidene chloride, vinyl bromide, vinyl iodide, vinyl acetate, vinyl propionate, vinyl benzoate, methyl methacrylate, ethyl methacrylate, propyl methacrylate, butyl methacrylate, n-octyl methacrylate, dodecyl methacrylate, 2-ethylhexyl methacrylate, stearyl methacrylate, behenyl methacrylate, phenyl methacrylate, dimethylaminoethyl methacrylate, diethylaminoethyl methacrylate, methyl acrylate, ethyl acrylate, n-butyl acrylate, isobutyl acrylate, propyl acrylate, n-octyl acrylate, dodecyl acrylate, 2-ethylhexyl acrylate, stearyl acrylate, behenyl acrylate, 2-chloroethyl acrylate, phenyl acrylate, methyl vinyl ether, ethyl vinyl ether, isobutyl vinyl ether, methyl vinyl ketone, hexyl vinyl ketone, methyl isopropenyl ketone, vinyl naphthalene, acrylonitrile, methacrylonitrile and acrylamides.

As the resin usable in the pigment composition of the present invention, it may be selected according to the use purposes of the pigment composition, and there are no particular limitations thereon. Stated specifically, it may include, e.g., polystyrene resin, styrene copolymers, polyacrylic acid resin, polymethacrylic acid resin, polyacrylate resin, polymethacrylate resin, acrylate copolymers, methacrylate copolymers, polyester resin, polyvinyl ether resin, polyvinyl alcohol resin and polyvinyl butyral resin. Besides, it may include polyurethane resins and polypeptide resins.

Any of these dispersion mediums may also be used in the form of a mixture of two or more types. The pigment composition produced by the wet process may be isolated by, e.g., filtration, decantation or centrifugation. The solvent may be removed by washing.

An auxiliary agent may further be added to the pigment composition of the present invention when it is produced. Stated specifically, it is, e.g., a surface-active agent, a pigment and non-pigment dispersant, a filler, a standardizing agent (standardizer), a resin, a wax, an anti-foaming agent, an anti-static agent, a dust proofing agent, a thickening agent, a shading colorant, a preservative, a drying preventive, a rheology control additive, a wetting agent, an antioxidant, a UV absorber or a light stabilizer, or a combination of any of these. The pigment dispersant of the present invention may also beforehand be added when a crude pigment is produced.

The pigment dispersion (pigment disperse system) of the present invention is described next. The pigment dispersion of the present invention is composed of the pigment composition described above and a non-water-soluble solvent. The pigment composition may be dispersed in the non-water-soluble solvent, or the respective constituents for the pigment composition may be dispersed in the non-water-soluble solvent. Stated specifically, it may be obtained in the following way, for example. The pigment dispersant and a resin are optionally dissolved into the non-water-soluble solvent, and a pigment or pigment composition powder is slowly added thereto with stirring to well adapt it to the non-water-soluble solvent. Further, a mechanical shear force is applied by using a dispersion machine such as a ball mill, a paint shaker, a dissolver, an attritor, a sand mill or a high-speed mill, whereby the pigment dispersant can be adsorbed to particle surfaces of the pigment and the pigment can stably be dispersed in the form of uniform fine particles.

As the non-water-soluble solvent usable in the pigment dispersion of the present invention, it may be selected according to the use purposes of the pigment composition, and there are no particular limitations thereon. It may specifically include, e.g., esters such as methyl acetate, ethyl acetate and propyl acetate; hydrocarbons such as hexane, octane, petroleum ether, cyclohexane, benzene, toluene and xylene; and halogen-containing hydrocarbons such as carbon tetrachloride, trichloroethylene and tetrabromoethane.

The non-water-soluble solvent usable in the pigment dispersion of the present invention may also be a polymerizable monomer. Stated specifically, it may include styrene, o-, m- or p-methylstyrene, o-, m- or p-ethylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, ethylene, propylene, butylene, isobutylene, vinyl chloride, vinylidene chloride, vinyl bromide, vinyl iodide, vinyl acetate, vinyl propionate, vinyl benzoate, methyl methacrylate, ethyl methacrylate, propyl methacrylate, n-octyl methacrylate, dodecyl methacrylate, 2-ethylhexyl methacrylate, stearyl methacrylate, phenyl methacrylate, dimethylaminoethyl methacrylate, diethylaminoethyl methacrylate, methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, phenyl acrylate, methyl vinyl ether, ethyl vinyl ether, isobutyl vinyl ether, methyl vinyl ketone, hexyl vinyl ketone, methyl isopropenyl ketone, vinyl naphthalene, acrylonitrile, methacrylonitrile and acrylamides.

The term "non-water-soluble solvent" used herein is also inclusive of substantially non-water-soluble solvents or only "slightly water-soluble" solvents which may commonly be so termed.

As the resin usable in the pigment dispersion of the present invention, it may be selected according to the use purposes of the pigment composition, and there are no particular limitations thereon. Stated specifically, it may include, e.g., polystyrene resin, styrene copolymers, polyacrylic acid resin, polymethacrylic acid resin, polyacrylate resin, polymethacrylate resin, acrylate copolymers, methacrylate copolymers, polyester resin, polyvinyl ether resin, polyvinyl alcohol resin and polyvinyl butyral resin. Besides, it may include polyurethane resins and polypeptide resins. Any of these resins may also be used in the form of a mixture of two or more types.

The toner of the present invention is described next in detail. In a toner having toner particles containing at least a binder resin and a colorant, the pigment composition of the present invention may also be used as the colorant. In virtue of the use of the pigment composition of the present invention in the toner, the dispersibility of the colorant in toner particles is well kept, and hence the toner is provided that affords a good color tone.

As the colorant of the toner particles constituting the toner of the present invention, the pigment composition of the present invention is always used, which pigment composition, however, may be used in combination with other colorant as long as the effect of improving pigment dispersibility that attributes to the pigment dispersant of the present invention is not inhibited.

Stated specifically, it may include, e.g., pigments or dyes such as C.I. Pigment Yellow 109, 110, 129, 147, 185; and C.I. Solvent Yellow 9, 17, 24, 31, 35, 58, 93, 100, 102, 103, 105, 112, 162, 163.

As the binder resin used in the toner particles constituting the toner of the present invention, usable are vinyl resins such as styrene-acrylic resins, polyester resin, or hybrid resins formed by combining any of them.

In a method of obtaining the toner particles directly by polymerization, a monomer for forming them is used. Stated specifically, preferably usable are styrene monomers such as styrene, o-, m- or p-methylstyrene, and o-, m- or p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile and acrylic acid amide; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile and methacrylic acid amide; and olefinic monomers such as butadiene, isoprene and cyclohexene. Any of these may be used alone, or may commonly be used in the form of an appropriate mixture of monomers which are so mixed that the theoretical glass transition temperature as described in NPL 9, may stand in the range of from 40° C. to 75° C. Appropriately so mixing monomers that the theoretical glass transition temperature may stand in the range of from 40° C. to 75° C. enables more improvement in storage stability of the toner, in image stability during printing on a large number of sheets, and in sharpness of images in full-color images.

Further, in the present invention, in order to enhance the mechanical strength of the toner particles and also control the molecular weight of the binder resin, a cross-linking agent may also be used when the binder resin is synthesized.

As the cross-linking agent used in the toner particles constituting the toner of the present invention, it may include, as a bifunctional cross-linking agent, divinylbenzene, 2,2-bis(4-acryloxyethoxyphenyl)propane, 2,2-bis(4-methacryloxyphenyl)propane, diallyl phthalate, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates, and the above diacrylates each acrylate moiety of which has been replaced with methacrylate.

As a polyfunctional cross-linking agent, it may include pentaerythritol triacrylate, trimethylolethane triacrylate, trimethylolpropane triacrylate, tetramethylolmethane tetraacrylate, oligoester acrylate, and methacrylates of these, and also triallyl cyanurate, triallyl isocyanurate and triallyl trimellitate.

Any of these cross-linking agents may preferably be added in an amount of from 0.05 part by mass to 10.0 parts by mass, and much preferably from 0.100 part by mass to 5.00 parts by mass, based on 100 parts by mass of the monomer.

The toner particles constituting the toner of the present invention may be incorporated with a wax component. The wax component may specifically include petroleum waxes such as paraffin wax, microcrystalline wax and petrolatum, and derivatives thereof; montan wax and derivatives thereof; hydrocarbon waxes obtained by Fischer-Tropsch synthesis, and derivatives thereof; polyolefin waxes as typified by polyethylene wax, and derivatives thereof; and naturally occurring waxes such as carnauba wax and candelilla wax, and derivatives thereof. The derivatives of these include oxides, block copolymers with vinyl monomers, and graft modified products. It may further include alcohols such as higher aliphatic alcohols, fatty acids such as stearic acid and palmitic acid, acid amide waxes, fatty ester, hardened caster oil and derivatives thereof, vegetable waxes, and animal waxes. Any of these may be used alone or in combination.

The wax component may preferably be added in such an amount that its content based on 100 parts by mass of the binder resin is in the range of from 2.5 parts by mass to 15.0 parts by mass, and much preferably in the range of from 3.0 parts by mass to 10.0 parts by mass, in total mass. Inasmuch as the wax component is added in an amount ranging from 2.5 parts by mass to 15.0 parts by mass based on 100 parts by mass of the binder resin, oilless fixing can be performed without any influence of the wax component on charge characteristics of the toner.

The toner particles constituting the toner of the present invention may be used in the state they are optionally incorporated with a charge control agent in order to control optimum triboelectric charge quantity in accordance with any development system. Such a charge control agent may include, e.g., monoazo metal compounds, boron compounds, quaternary ammonium salts, carixarene, silicon compounds, aromatic hydroxycarboxylic acids, and metal salts, anhydrides and esters of these. Also, a resin into which such a charge control agent has been introduced may internally be added to the toner particles.

To the toner particles constituting the toner of the present invention, an inorganic fine powder may externally be added as a fluidizing agent. Such a fluidizing agent may include, e.g., fine powders of silica, titania, alumina, double oxides of any of them, and any of these having been surface-treated.

The toner of the present invention may be either of a magnetic toner and a non-magnetic toner. Where it is used as the magnetic toner, the toner particles constituting the toner of the present invention may be used in the state they are incorporated with a magnetic material. Such a magnetic material may include iron oxides such as magnetite, maghemite and ferrite, and iron oxides including other metal oxides; metals such as Fe, Co and Ni, or alloys of any of these metals with any of metals such as Al, Co, Cu, Pb, Mg, Ni, Sn, Zn, Sb, Be, Bi, Cd, Ca, Mn, Se, Ti, W and V, and mixtures of any of these.

As a process for producing the toner particles constituting the toner of the present invention, any of all process conventionally used may be used. Stated specifically, it may include pulverization, suspension polymerization and emulsion polymerization.

In the present invention, the toner may preferably have a weight-average particle diameter (hereinafter also "D4") of from 3.0 μm to 15.0 μm, and much preferably from 4.0 μm to 12.0 μm. As long as it has a D4 of from 3.0 μm to 15.0 μm, the toner is preferable as being stably chargeable when used in electrophotographic systems, as less causing any fog or spots of toner around line images when development is continuously operated on a large number of sheets (running operation), and also preferable in view of color reproducibility in halftone areas.

If the toner has a D4 of less than 3.0 μm, it can not stably be chargeable with ease when used in electrophotographic systems, and tends to cause fog or spots of toner around line images when development is continuously operated on a large number of sheets (running operation). If the toner has a D4 of more than 15.0 μm, a greatly low color reproducibility in halftone areas may result, and the images obtained may result in images with unevenness on their surfaces, undesirably.

The toner of the present invention may also preferably have a ratio of D4 to number-average particle diameter (D1), D4/D1, of 1.35 or less, and much preferably 1.30 or less. Where its D4/D1 is 1.35 or less, the toner can much more less cause fog or lower in transfer performance, and also can enjoy high resolution with ease.

Incidentally, the D4 and D1 of the toner of the present invention may differ in how to control them, depending on how to produce the toner particles. For example, in the case of suspension polymerization, they may be controlled by controlling the concentration of a dispersant used when an aqueous dispersion medium is prepared, the rate of reaction and stirring, the time for reaction and stirring, and so forth.

EXAMPLES

The present invention is described below in greater detail by giving working examples, to which, however, the present invention is by no means limited. In the following, "part(s)" and "%" are by mass unless particularly noted.

Example 1

Azo compounds represented by the formula (1) were obtained in the following way.

Synthesis Example 1

Synthesis of Compound (38)

A compound (38) in which, in the formula (1), $R_1$ to $R_4$, $R_6$, $R_7$, $R_9$, $R_{11}$, $R_{13}$ and $R_{15}$ are hydrogen atoms, $R_{12}$ and $R_{14}$ are $L_2R_{21}R_{22}$ groups, where $L_2$ is a carboxylic acid tertiary amide group and $R_{21}$ and $R_{22}$ are 2-ethylhexyl groups, $R_5$ and $R_8$ are $COOR_{17}$ groups, and $R_{10}$, $R_{16}$ and $R_{17}$ are methyl groups was synthesized according to the following synthesis scheme.

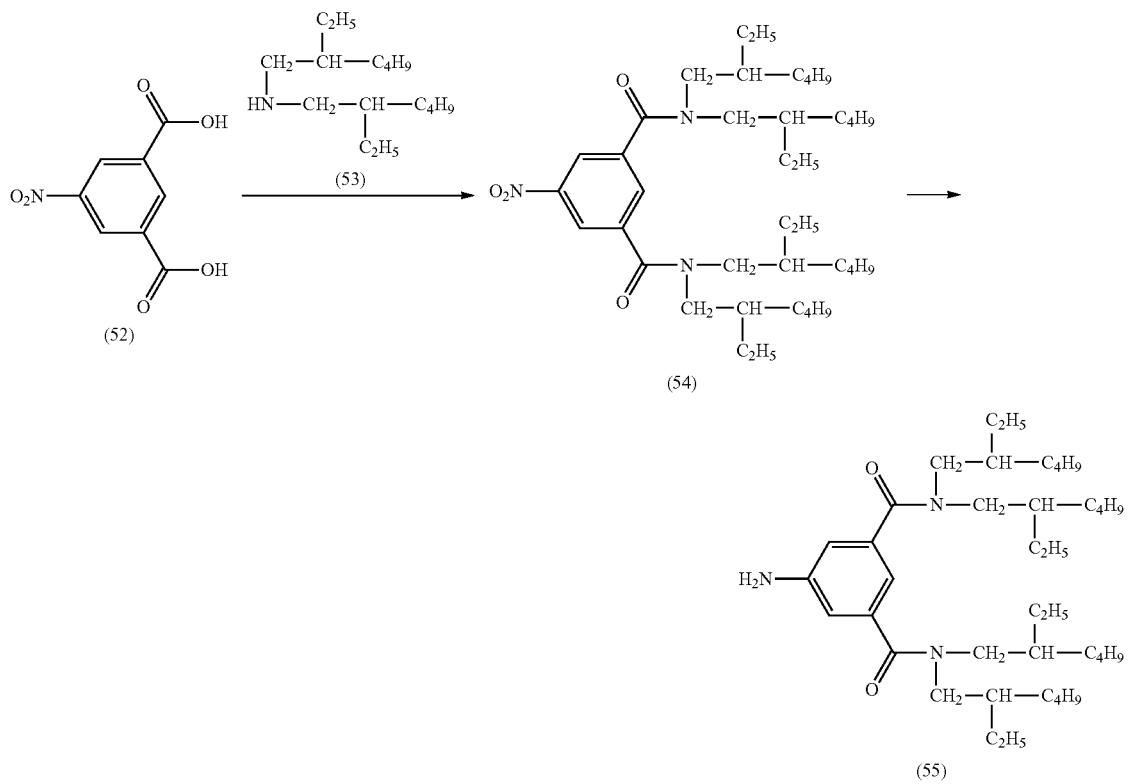

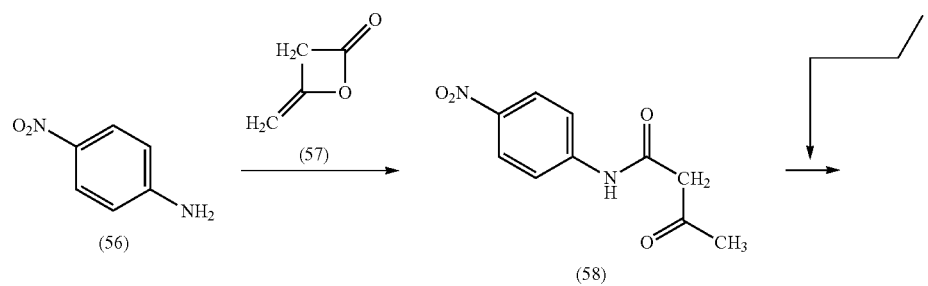
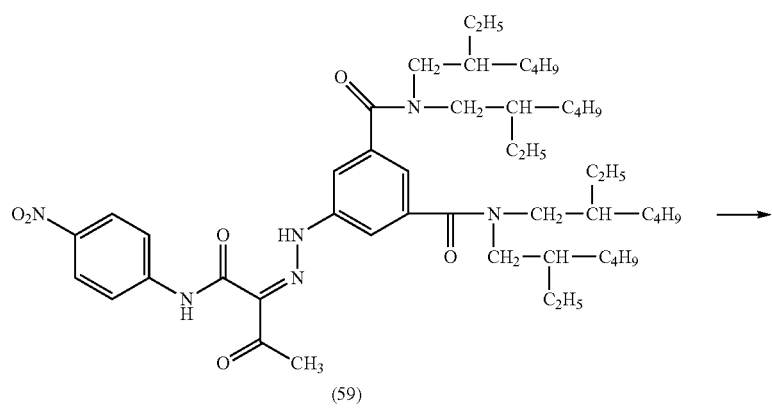
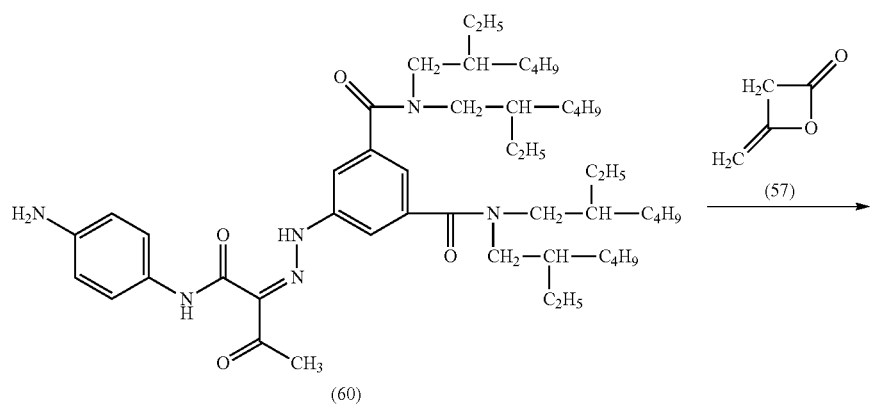
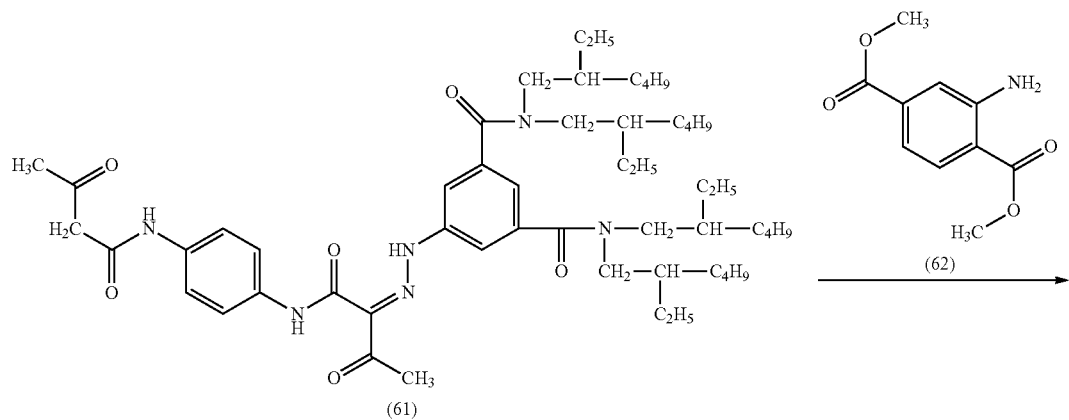

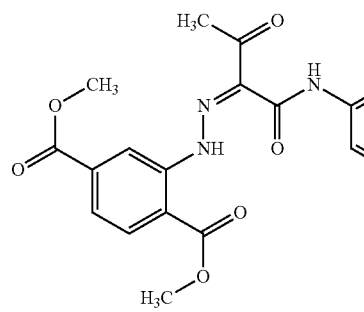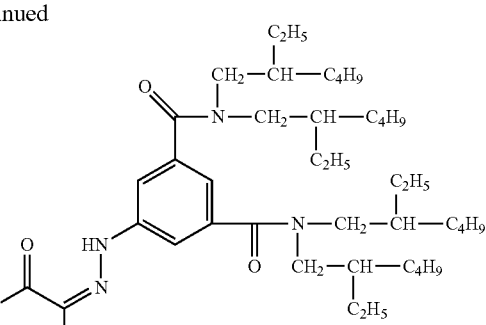

(38)

First, a compound (54) was synthesized by using compounds (52) and (53). To 50.00 parts of chloroform, 5.00 parts of the compound (52) was added, and these were ice-cooled to 10° C. or below, where 11.00 parts of thionyl chloride was added thereto. Thereafter, the mixture obtained was stirred at 65° C. for 3 hours. This was again ice-cooled to 10° C. or below, and then 11.70 parts of the compound (53) and 6.00 parts of triethylamine were added thereto. Thereafter, the mixture obtained was stirred at 65° C. for 3 hours. After the reaction was completed, the reaction product obtained was extracted with chloroform, and then purified by column chromatography (eluting solution: ethyl acetate/heptane) to obtain 13.00 parts of the compound (54) as an intermediate (yield: 83.4%).

Next, a compound (55) was synthesized by using the compound (54). To 20.00 parts of N,N-dimethylformamide, 12.00 parts of the compound (54) and 0.400 part of palladium-activated carbon (palladium: 5%) were added, and the mixture obtained was stirred at room temperature for 4 hours in an atmosphere of hydrogen gas (reaction pressure: 0.1 to 0.4 MPa). After the reaction was completed, the solution obtained was separated by filtration, and then concentrated to obtain 11.00 parts of the compound (55) (yield: 96.0%).

Next, a compound (58) was synthesized by using compounds (56) and (57). To 30.00 parts of chloroform, 5.00 parts of the compound (56) was added, and these were ice-cooled to 10° C. or below, where 3.20 parts of the compound (57) was added thereto. Thereafter, the mixture obtained was stirred at 65° C. for 2 hours. After the reaction was completed, the reaction product obtained was extracted with chloroform, and then concentrated to obtain 7.60 parts of the compound (58) (yield: 94.5%).

Next, a compound (59) was synthesized by using the compounds (55) and (58). To 10.00 parts of the compound (55), 50.00 parts of methanol and 4.29 parts of concentrated hydrochloric acid were added, and these were ice-cooled to 10° C. or below. To the solution obtained, a solution obtained by dissolving 1.60 parts of sodium nitrite in 3.50 parts of water was added to carry out reaction at the same temperature as the above for 1 hour. Then, 0.77 part of sulfamic acid was added to the reaction mixture, which was further stirred for 20 minutes (a diazonium salt solution). To 50.00 parts of methanol, 3.54 parts of the compound (58) was added, and these were ice-cooled to 10° C. or below, where the diazonium salt solution was added thereto. Thereafter, a solution obtained by dissolving 4.60 parts of sodium acetate in 5.00 parts of water was added to carry out reaction at 10° C. or below for 2 hours. After the reaction was completed, the reaction product obtained was extracted with chloroform, and then concentrated to obtain 11.5 parts of the compound (59) (yield: 83.9%).

Next, a compound (60) was synthesized by using the compound (59). To 20.00 parts of N,N-dimethylformamide, 11.00 parts of the compound (59) and 0.40 part of palladium-activated carbon (palladium: 5%) were added, and the mixture obtained was stirred at room temperature for 4 hours in an atmosphere of hydrogen gas (reaction pressure: 0.1 to 0.4 MPa). After the reaction was completed, the solution obtained was separated by filtration, and then concentrated to obtain 9.00 parts of the compound (60) (yield: 84.8%).

Next, a compound (61) was synthesized by using the compounds (60) and (57). To 50.00 parts of chloroform, 8.50 parts of the compound (60) was added, and these were ice-cooled to 10° C. or below, where 0.90 part of the compound (57) was added thereto. Thereafter, the mixture obtained was stirred at 65° C. for 2 hours. After the reaction was completed, the reaction product obtained was extracted with chloroform, and then concentrated to obtain 8.50 parts of the compound (61) (yield: 90.8%).

Next, the compound (38) was synthesized by using the compound (61) and a compound (62). To 1.83 parts of the compound (62), 20.00 parts of methanol and 2.29 parts of concentrated hydrochloric acid were added, and these were ice-cooled to 10° C. or below. To the solution obtained, a solution obtained by dissolving 0.90 part of sodium nitrite in 2.00 parts of water was added to carry out reaction at the same temperature as the above for 1 hour. Then, 0.42 part of sulfamic acid was added to the reaction mixture, which was further stirred for 20 minutes (a diazonium salt solution). To 80.00 parts of methanol, 8.00 parts of the compound (61) was added, and these were ice-cooled to 10° C. or below, where the diazonium chloride solution was added thereto. Thereafter, a solution obtained by dissolving 2.50 parts of sodium acetate in 5.00 parts of water was added to carry out reaction at 10° C. or below for 2 hours. After the reaction was completed, the reaction product obtained was extracted with chloroform, and then purified by column chromatography to obtain 8.20 parts of the compound (38) (yield: 82.6%).

The results of analysis of the compound (38) obtained are shown below.

Results of analysis of the compound (38):

(1) Results of nuclear magnetic resonance spectroscopy ($^1$H-NMR) (400 MHz, CDCl$_3$, room temperature 25° C.) (see FIG. 1):

δ[ppm]=15.56 (1H, s), 14.72 (1H, s), 11.36 (1H, s), 11.34 (1H, s), 8.54 (1H, s), 8.08 (1H, d), 7.73 (1H, d), 7.67 (2H, d), 7.56 (2H, d), 7.33 (2H, s), 7.00 (1H, s), 4.0 (3H, s), 3.91 (3H, s), 3.3 (4H, s), 3.11 (4H, s), 2.61 (3H, s), 2.48 (3H, s), 1.74 (2H, s), 1.43-0.96 (32H, m), 0.95-0.59 (24H, m)

(2) Results of mass spectrometry (ESI-TOF MS):

m/z of (M-H)$^-$=1133.7 where (M-H)$^-$ represents a proton elimination ion of the compound (38).

(3) Results of HPLC analysis:
Purity: 99.0 area %; retention time: 19.6 minutes;
electron absorption spectrum λmax: 382 nm (solvent: methanol)

Synthesis Example 2

Synthesis of Compound (39)

A compound (39) in which, in the formula (1), $R_1$ to $R_4$, $R_6$, $R_7$, $R_9$, $R_{11}$, $R_{14}$ and $R_{15}$ are hydrogen atoms, $R_{12}$ and $R_{13}$ are $L_1R_{20}$ groups, where $L_1$ is a carboxylate group and $R_{20}$ is a 2-ethylhexyl group, $R_5$ and $R_8$ are COOR$_{17}$ groups, and $R_{10}$, $R_{16}$ and $R_{17}$ are methyl groups was synthesized according to the following synthesis scheme.

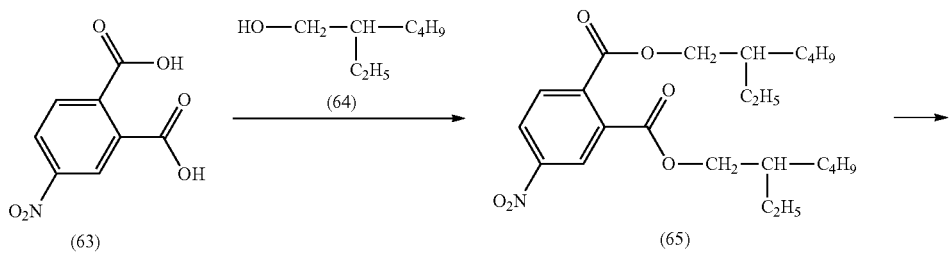

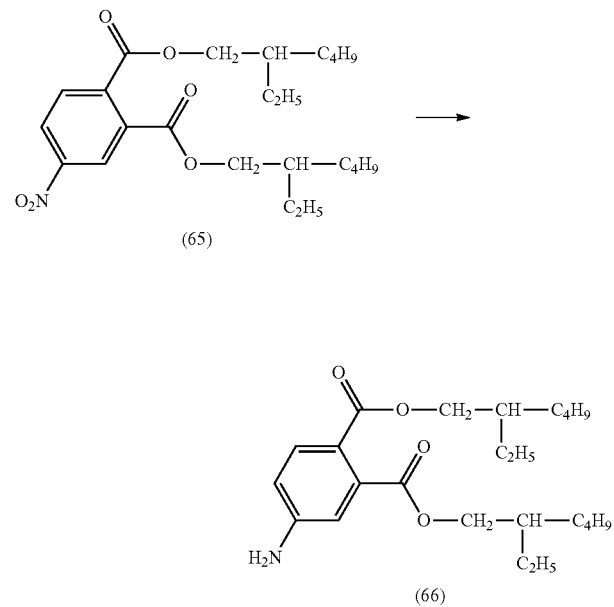

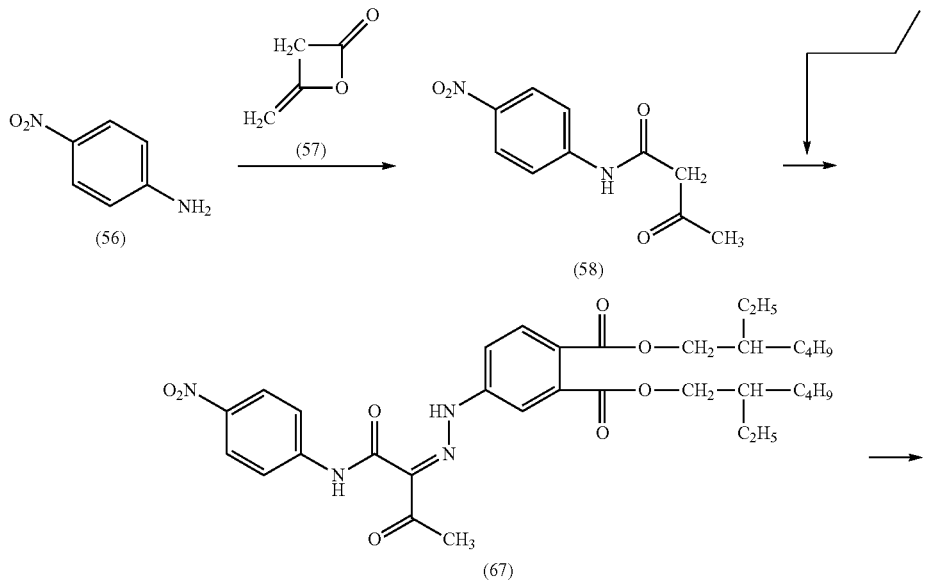

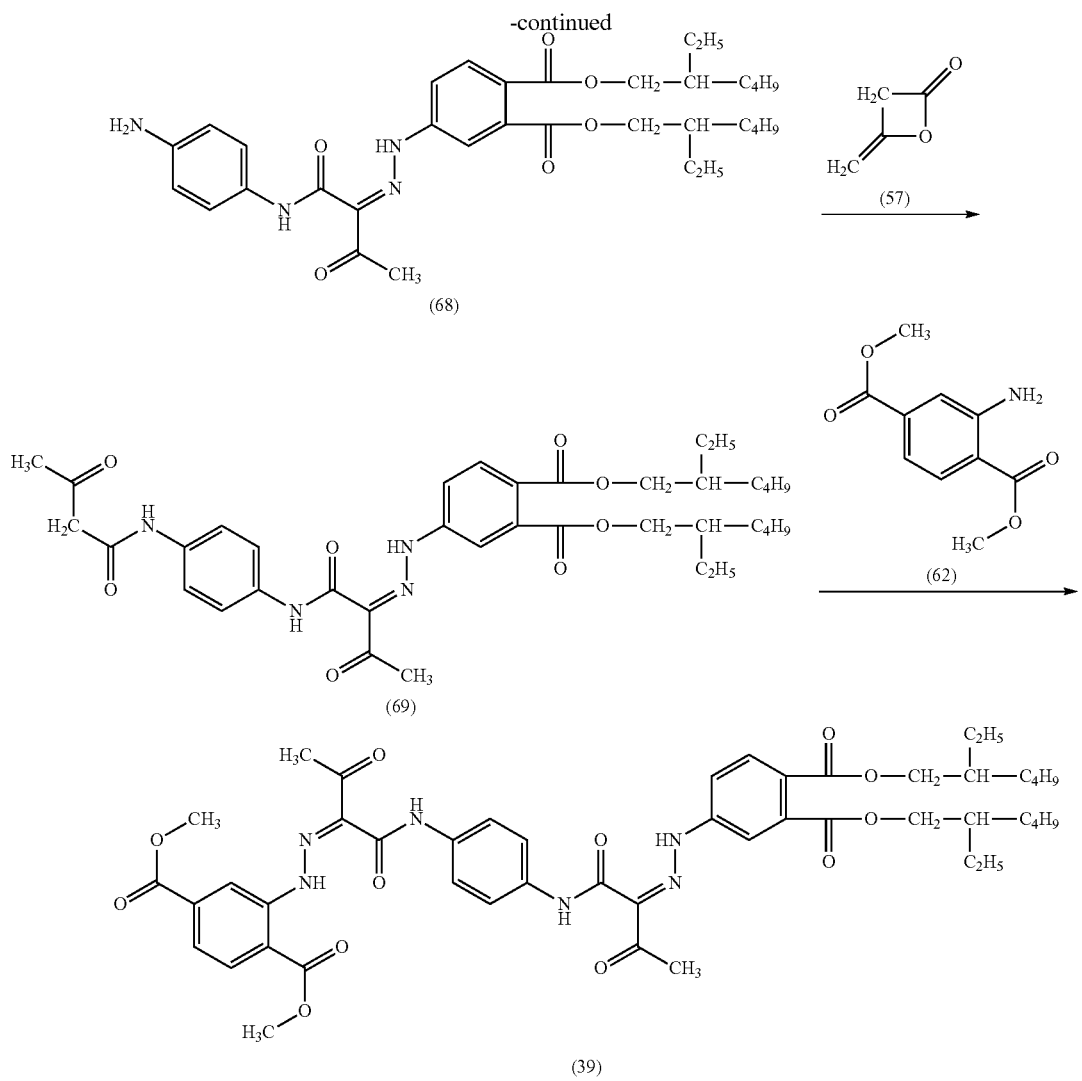

First, a compound (65) was synthesized by using compounds (63) and (64). 8.74 parts of the compound (63), 16.18 parts of the compound (64) and 0.12 part of tetraisopropoxytitanium were put together, and the mixture obtained was stirred at 150° C. for 4 hours. After the reaction was completed, any unreacted compound (64) was separated off by distillation under reduced pressure, and thereafter the reaction product obtained was extracted with chloroform, and then concentrated to obtain 15.30 parts of the compound (65) (yield: 86.0%).

Next, a compound (66) was synthesized by using the compound (65). To 20.00 parts of N,N-dimethylformamide, 12.00 parts of the compound (65) and 0.60 part of palladium-activated carbon (palladium: 5%) were added, and the mixture obtained was stirred at room temperature for 4 hours in an atmosphere of hydrogen gas (reaction pressure: 0.1 to 0.4 MPa). After the reaction was completed, the solution obtained was separated by filtration, and then concentrated to obtain 10.00 parts of the compound (66) (yield: 89.5%).

Next, a compound (58) was synthesized in the same way as that in the above Synthesis Example 1.

Next, a compound (67) was synthesized by using the compounds (66) and (58). To 9.00 parts of the compound (66), 50.00 parts of methanol and 5.80 parts of concentrated hydrochloric acid were added, and these were ice-cooled to 10° C. or below. To the solution obtained, a solution obtained by dissolving 2.30 parts of sodium nitrite in 4.60 parts of water was added to carry out reaction at the same temperature as the above for 1 hour. Then, 1.10 parts of sulfamic acid was added to the reaction mixture, which was further stirred for 20 minutes (a diazonium salt solution). To 50.00 parts of methanol, 5.00 parts of the compound (58) was added, and these were ice-cooled to 10° C. or below, where the diazonium salt solution was added thereto. Thereafter, a solution obtained by dissolving 6.40 parts of sodium acetate in 7.00 parts of water was added to carry out reaction at 10° C. or below for 2 hours. After the reaction was completed, the reaction product obtained was extracted with chloroform, and then concentrated to obtain 12.50 parts of the compound (67) (yield: 88.2%).

Next, a compound (68) was synthesized by using the compound (67). To 20.00 parts of N,N-dimethylformamide, 11.00 parts of the compound (67) and 0.50 part of palladium-activated carbon (palladium: 5%) were added, and the mixture obtained was stirred at room temperature for 4 hours in an atmosphere of hydrogen gas (reaction pressure: 0.1 to 0.4 MPa). After the reaction was completed, the solution obtained was separated by filtration, and then concentrated to obtain 9.30 parts of the compound (68) (yield: 88.7%).

Next, a compound (69) was synthesized by using the compound (68) and a compound (57). To 50.00 parts of chloroform, 8.50 parts of the compound (68) was added, and these were ice-cooled to 10° C. or below, where 1.23 parts of the compound (57) was added thereto. Thereafter, the mixture obtained was stirred at 65° C. for 2 hours. After the reaction was completed, the reaction product obtained was extracted with chloroform, and then concentrated to obtain 9.00 parts of the compound (69) (yield: 93.0%).

Next, the compound (39) was synthesized by using the compound (69) and a compound (62). To 2.00 parts of the compound (62), 20.00 parts of methanol and 3.00 parts of concentrated hydrochloric acid were added, and these were ice-cooled to 10° C. or below. To the solution obtained, a solution obtained by dissolving 1.20 parts of sodium nitrite in 3.00 parts of water was added to carry out reaction at the same temperature as the above for 1 hour. Then, 0.56 part of sulfamic acid was added to the reaction mixture, which was further stirred for 20 minutes (a diazonium salt solution). To 80.00 parts of methanol, 8.00 parts of the compound (69) was added, and these were ice-cooled to 10° C. or below, where the diazonium chloride solution was added thereto. Thereafter, a solution obtained by dissolving 3.30 parts of sodium acetate in 5.00 parts of water was added to carry out reaction at 10° C. or below for 2 hours. After the reaction was completed, the reaction product obtained was extracted with chloroform, and then purified by column chromatography to obtain 9.10 parts of the compound (39) (yield: 86.3%).

The results of analysis of the compound (39) obtained are shown below.

Figure 2:
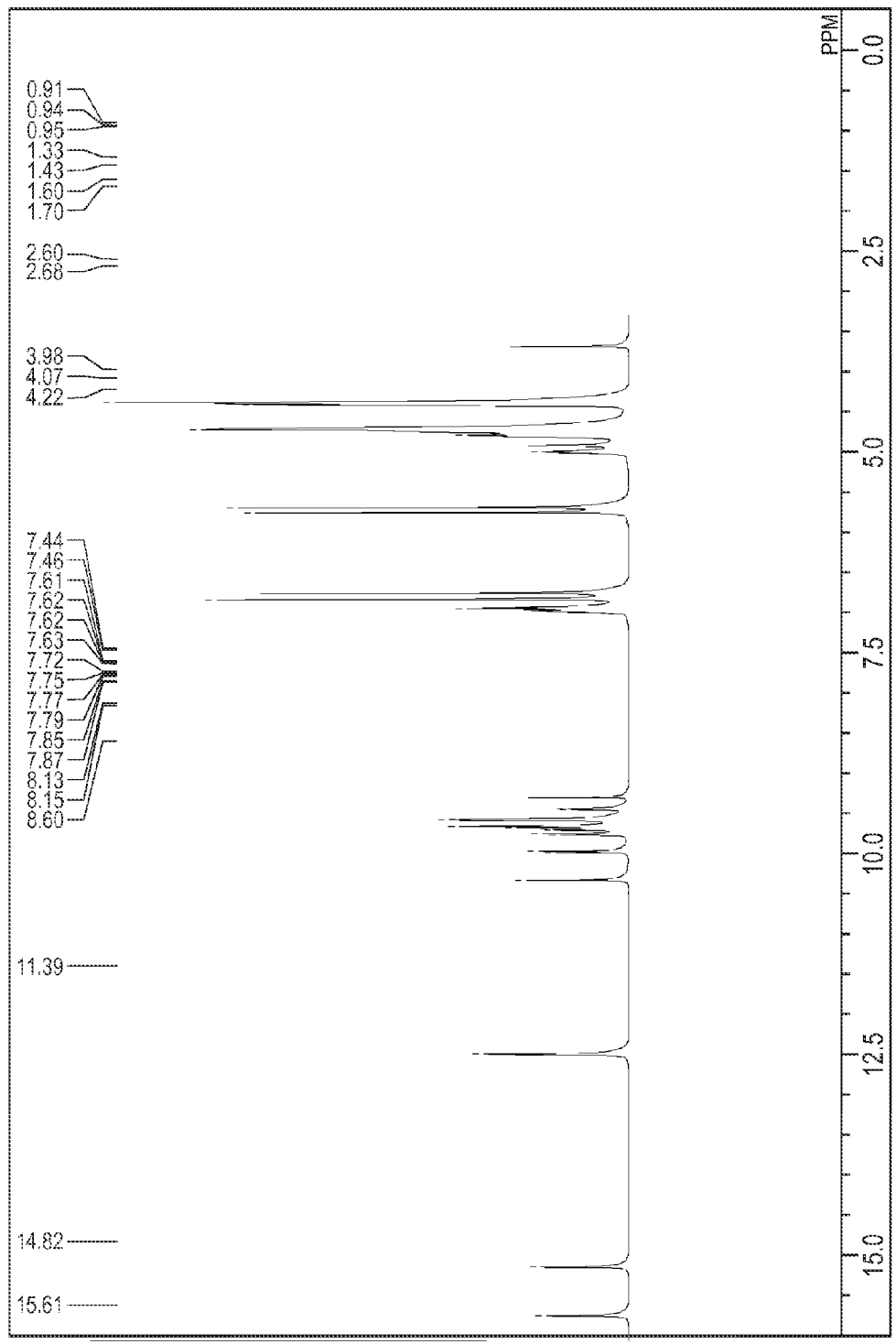
FIG. 2 is a graph showing a $^1$H-NMR spectrum of a compound (39) of the present invention.

Results of analysis of the compound (39):

(1) Results of nuclear magnetic resonance spectroscopy ($^1$H-NMR) (400 MHz, CDCl$_3$, room temperature 25° C.) (see FIG. 2):

δ[ppm]=15.61 (1H, s), 14.82 (1H, s), 11.39 (2H, s), 8.60 (1H, s), 8.14 (1H, d), 7.86 (1H, d), 7.78 (1H, d), 7.73 (2H, d), 7.62 (1H, s), 7.62 (2H, d), 4.33-4.14 (4H, m), 4.07 (3H, s), 3.98 (3H, s), 2.68 (3H, s), 2.60 (3H, s), 1.80-1.63 (2H, m), 1.60 (2H, s), 1.47-1.19 (16H, m), 0.98-0.75 (12H, m)

(2) Results of mass spectrometry (ESI-TOF MS):

m/z of (M-H)$^-$=911.4 where (M-H)$^-$ represents a proton elimination ion of the compound (39).

(3) Results of HPLC analysis:

Purity: 99.0 area %; retention time: 20.8 minutes; electron absorption spectrum λmax: 384 nm (solvent: methanol)

Preparation of Pigment Dispersions

Pigment dispersions (pigment disperse systems) of the present invention were prepared in the following way.

Pigment Dispersion

Preparation Example 1

Using 18.00 parts of the pigment represented by the formula (2) as an azo pigment, 1.80 parts of the compound (18) as a pigment dispersant and 180.00 parts of styrene as a non-water-soluble solvent, these were mixed together with 130 parts of glass beads (diameter: 1 mm), and the mixture obtained was further put to dispersion treatment by means of an attritor (manufactured by Nippon Coke & Engineering Co., Ltd.) for 3 hours, followed by filtration with a mesh to obtain a pigment dispersion (101).

Pigment Dispersion

Preparation Example 2

The procedure in Pigment Dispersion Preparation Example 1 was repeated except that the compounds (18) was changed for the compounds (19) to (51), to obtain pigment dispersions (102) to (134), respectively.

Pigment Dispersion

Preparation Example 3

The procedure in Pigment Dispersion Preparation Example 1 was repeated except that the pigment represented by the formula (2) was changed for a pigment represented by the following formula (70) and the compounds (18) was changed for the compound (38), to obtain a pigment dispersion (135).

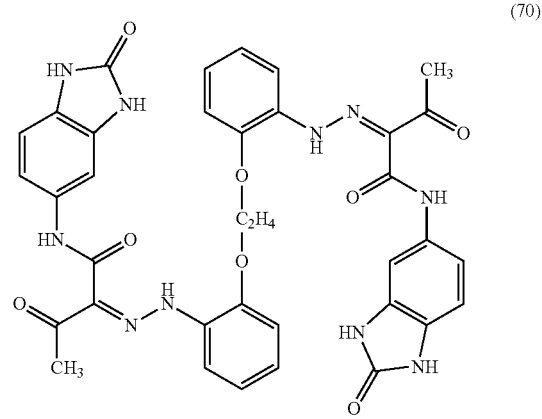

(70)

Pigment Dispersion

Preparation Example 4

The procedure in Pigment Dispersion Preparation Example 1 was repeated except that the pigment represented by the formula (2) was changed for a pigment represented by the following formula (71) and the compound (18) was changed for the compound (38), to obtain a pigment dispersion (136).

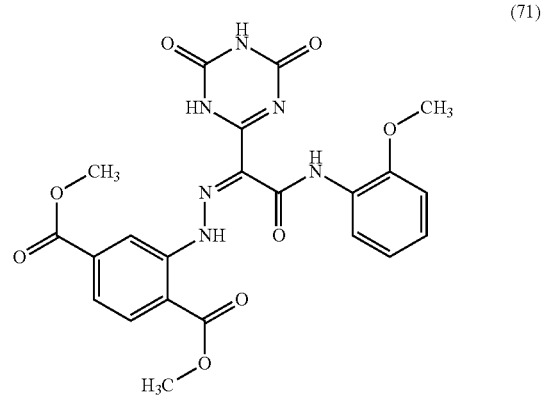 [SMILES: COC(=O)c1ccc(C(=O)OC)c(N/N=C(\C(=O)Nc2ccccc2OC)c2nc(=O)[nH]c(=O)[nH]2)c1]

(71)

Pigment Dispersion

Preparation Example 5

The procedure in Pigment Dispersion Preparation Example 1 was repeated except that the compound (18) was changed for the compound (38) and the styrene monomer was changed for butyl acrylate, to obtain a pigment dispersion (137).

Pigment Dispersion

Preparation Example 6

The procedure in Pigment Dispersion Preparation Example 1 was repeated except that the compound (18) was changed for the compound (38) and the styrene monomer was changed for toluene, to obtain a pigment dispersion (138).

Preparation of Comparative Pigment Dispersions

Comparative pigment dispersions (pigment disperse systems for comparison) were prepared in the following way.

Comparative Pigment Dispersion

Preparation Example 1

The procedure in Pigment Dispersion Preparation Example 1 was repeated except that the compound (18) was not added, to obtain a pigment dispersion (139) for comparison.

Comparative Pigment Dispersion

Preparation Example 2

The procedure in Pigment Dispersion Preparation Examples 3 and 4 each was repeated except that the compound (38) was not added, to obtain pigment dispersions (140) and (141), respectively, for comparison.

Comparative Pigment Dispersion

Preparation Example 3

The procedure in Pigment Dispersion Preparation Examples 5 and 6 each was repeated except that the compound (38) was not added, to obtain pigment dispersions (142) and (143), respectively, for comparison.

Comparative Pigment Dispersion

Preparation Example 4

The procedure in Pigment Dispersion Preparation Example 1 was repeated except that the compound (18) was changed for the following compound (72) for comparison, disclosed in PTL 3 listed previously, to obtain a pigment dispersion (144) for comparison.

(72)

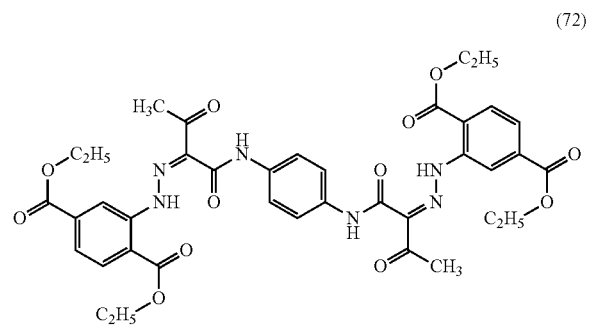 [SMILES: CCOC(=O)c1ccc(C(=O)OCC)c(N/N=C(/C(C)=O)C(=O)Nc2ccc(NC(=O)/C(=N\Nc3cc(C(=O)OCC)ccc3C(=O)OCC)C(C)=O)cc2)c1]

Comparative Pigment Dispersion

Preparation Example 5

The procedure in Pigment Dispersion Preparation Example 1 was repeated except that the compound (18) was changed for a compound (73) for comparison "SOLSPERSE (registered trademark; available from Lubrizol Corporation)", disclosed in PTL 2 listed previously, to obtain a pigment dispersion (145) for comparison.

Example 2

The azo compounds obtained in the present invention were evaluated in the following way.

Evaluation of Pigment Dispersibility

About the pigment dispersibility to which the compound represented by the formula (1) was to attribute, it was evaluated by the gloss of a coating film of each of the pigment dispersants obtained. More specifically, each pigment dispersant was drawn up with a syringe, and put on a sheet of art paper (SA Kanefuji Plus, 180 kg; available from Oji Paper Co., Ltd.) at its upper end portion in a linear form, which was then spread over the paper by using a wire bar (#10) so as to be uniformly coated. After the coating was dried, the gloss (reflection angle: 60°) of the coating film formed was measured with Gloss Meter VG2000 (manufactured by Nippon Denshoku Industries, Co., Ltd.). The more finely the pigment stands dispersed, the more the coating film is improved in smoothness to come improved in gloss. From this fact, the percentage of improvement in gloss of the coating film of the pigment dispersion to which the pigment dispersant was added was evaluated on the basis of gloss of a coating film of a pigment dispersion to which any pigment dispersant was not added, which was evaluated as shown below.

A: The percentage of improvement in gloss is 20% or more.
B: The percentage of improvement in gloss is 10% or more to less than 20%.
C: The percentage of improvement in gloss is 1% or more to less than 10%.
D: The percentage of improvement in gloss is less than 1%.

Here, as the pigment dispersion on the basis of which the evaluation was made, a pigment dispersion was chosen which contained the same types of non-water-soluble solvent and pigment except that it did not contain any pigment dispersant. Stated specifically, the percentages of improvement in gloss of the coating films of the pigment dispersions (101) to (134) was measured and evaluated on the basis of the gloss of the coating film of the pigment dispersion (139); the percentage of improvement in gloss of the coating film of the pigment dispersion (135), on the basis of the gloss of the coating film of the pigment dispersion (140); the percentage of improvement in gloss of the coating film of the pigment dispersion (136), on the basis of the gloss of the coating film of the pigment dispersion (141); the percentage of improvement in gloss of the coating film of the pigment dispersion (137), on the basis of the gloss of the coating film of the pigment dispersion (142); and the percentage of improvement in gloss of the coating film of the pigment dispersion (138), on the basis of the gloss of the coating film of the pigment dispersion (143).

The pigment dispersibility was judged to be good as long as the percentage of improvement in gloss is 10% or more.

The types of pigment dispersions, the types of pigment dispersants and the results of evaluation of pigment dispersibility of pigment dispersions are shown in Table 7.

Comparative Example 1

The pigment dispersibility of the pigment dispersions (139) to (145) each for comparison was evaluated in the same way as that in Example 2. The results of evaluation are shown in Table 7.

TABLE 7

Dispersibility Evaluation Results of Pigment Dispersions

| Pigment dispersion | Pigment dispersant | Non-water-soluble solvent | Pigment, Formula: | Pigment dispersibility |
|---|---|---|---|---|
| 101 | Compound (18) | Styrene monomer | (2) | B |
| 102 | Compound (19) | Styrene monomer | (2) | A |
| 103 | Compound (20) | Styrene monomer | (2) | A |
| 104 | Compound (21) | Styrene monomer | (2) | A |
| 105 | Compound (22) | Styrene monomer | (2) | A |
| 106 | Compound (23) | Styrene monomer | (2) | A |
| 107 | Compound (24) | Styrene monomer | (2) | A |
| 108 | Compound (25) | Styrene monomer | (2) | B |
| 109 | Compound (26) | Styrene monomer | (2) | B |
| 110 | Compound (27) | Styrene monomer | (2) | B |
| 111 | Compound (28) | Styrene monomer | (2) | B |
| 112 | Compound (29) | Styrene monomer | (2) | B |
| 113 | Compound (30) | Styrene monomer | (2) | B |
| 114 | Compound (31) | Styrene monomer | (2) | B |
| 115 | Compound (32) | Styrene monomer | (2) | B |
| 116 | Compound (33) | Styrene monomer | (2) | B |
| 117 | Compound (34) | Styrene monomer | (2) | B |
| 118 | Compound (35) | Styrene monomer | (2) | B |
| 119 | Compound (36) | Styrene monomer | (2) | B |
| 120 | Compound (37) | Styrene monomer | (2) | B |
| 121 | Compound (38) | Styrene monomer | (2) | A |
| 122 | Compound (39) | Styrene monomer | (2) | A |
| 123 | Compound (40) | Styrene monomer | (2) | A |
| 124 | Compound (41) | Styrene monomer | (2) | B |
| 125 | Compound (42) | Styrene monomer | (2) | B |
| 126 | Compound (43) | Styrene monomer | (2) | A |
| 127 | Compound (44) | Styrene monomer | (2) | A |
| 128 | Compound (45) | Styrene monomer | (2) | A |
| 129 | Compound (46) | Styrene monomer | (2) | A |
| 130 | Compound (47) | Styrene monomer | (2) | A |
| 131 | Compound (48) | Styrene monomer | (2) | A |
| 132 | Compound (49) | Styrene monomer | (2) | A |
| 133 | Compound (50) | Styrene monomer | (2) | A |
| 134 | Compound (51) | Styrene monomer | (2) | B |
| 135 | Compound (38) | Styrene monomer | (70) | B |
| 136 | Compound (38) | Styrene monomer | (71) | B |
| 137 | Compound (38) | Butyl acrylate | (2) | A |
| 138 | Compound (38) | Toluene | (2) | A |
| 139 | None | Styrene monomer | (2) | D |
| 140 | None | Styrene monomer | (70) | D |
| 141 | None | Styrene monomer | (71) | D |
| 142 | None | Butyl acrylate | (2) | D |
| 143 | None | Toluene | (2) | D |
| 144 | Cp. Comp. (72) | Styrene monomer | (2) | D |
| 145 | Cp. Comp. (73) | Styrene monomer | (2) | D |

Cp. Comp.: Compound for comparison

As is seen from Table 7, the azo compound of the present invention, when used in combination with azo pigments, affords pigment dispersions in which the azo pigments stand well dispersed. From this fact, it has been ascertained that the azo compound of the present invention is useful as a pigment dispersant for the azo pigments.

Pigment Dispersion

Preparation Example 7

Using 42.00 parts of the pigment represented by the formula (2) as an azo pigment and 4.20 parts of the compound (38) as a pigment dispersant, these were mixed by dry process by hybridization system NHS-0 (manufactured by Nara Machinery Co., Ltd.) to obtain a pigment composition.

18.00 parts of the obtained pigment composition and 180.00 parts of styrene were mixed. The mixture was further put to dispersion treatment by means of an attritor (manufactured by Nippon Coke & Engineering Co., Ltd.) for 1 hour, followed by filtration with a mesh to obtain a pigment dispersion.

The pigment dispersibility of the obtained pigment dispersion was evaluated in the same way as that in Example 2, it has been ascertained that the azo compound similarly has good pigment dispersibility for the obtained pigment dispersion.

Yellow Toner Particles

Production Example 1

Into a 2-liter four-necked flask having a high-speed stirrer TK-homomixer (manufactured by RIMIX Corporation), 710.00 parts of ion-exchanged water and 450.00 parts of an aqueous 0.1 mol/liter $Na_3PO_4$ solution was introduced, and these were heated to 60° C., controlling the number of revolutions at 12,000 rpm. To the mixture obtained, 68.00 parts of an aqueous 1.0 mol/liter $CaCl_2$ solution was slowly added to obtain an aqueous dispersion medium containing $Ca_3(PO_4)_2$ as a fine slightly water-soluble dispersion stabilizer.

The following components were heated to 60° C., and then uniformly dissolved or dispersed by means of the TK-homomixer and at 5,000 rpm.

Pigment dispersion (101): 132.00 parts
Styrene monomer: 46.00 parts
n-Butyl acrylate monomer: 34.00 parts
Polar resin: 10.00 parts
(polycondensation product of propylene oxide modified bisphenol A with isophthalic acid; glass transition temperature: 65° C.; Mw: 10,000; Mn: 6,000)
Ester wax: 25.00 parts
(peak temperature of maximum endothermic peak in DSC measurement: 70° C.; Mn: 704)
Salicylic acid aluminum compound: 2.0 parts (BONTRON E-88, available from Orient Chemical Industries, Ltd.)
Divinylbenzene monomer: 0.10 part In this, 10 parts of a polymerization initiator 2,2'-azobis(2,4-dimethylvaleronitrile) was dissolved to prepare a polymerizable monomer composition. This polymerizable monomer composition was introduced into the above aqueous dispersion medium to carry out granulation for 15 minutes while keeping a number of revolutions of 12,000 rpm. Thereafter, the high-speed stirrer was changed for a stirrer having propeller stirring blades, and, keeping its liquid temperature at 60° C., the polymerization was continued for 5 hours. Thereafter, the liquid temperature was raised to 80° C., and the polymerization was continued for 8 hours. After the polymerization was completed, residual monomers were evaporated off at 80° C. under reduced pressure, followed by cooling to 30° C. to obtain a fine polymer particle fluid dispersion.

Next, the fine polymer particle fluid dispersion was moved to a washing container, and diluted hydrochloric acid was added thereto with stirring. With adjustment of pH to 1.5, the mixture obtained was stirred for 2 hours to dissolve a compound of phosphoric acid and calcium, containing $Ca_3(PO_4)_2$, followed by solid-liquid separation by means of a filter to obtain fine polymer particles. This was introduced into water and stirred to make them again into a fluid dispersion, followed by solid-liquid separation by means of the filter. The re-dispersion of fine polymer particles and the solid-liquid separation were repeatedly carried out until the compound of phosphoric acid and calcium, containing $Ca_3(PO_4)_2$, was sufficiently removed. Thereafter, the fine polymer particles having finally been solid-liquid separated were sufficiently dried by means of a dryer to obtain yellow toner particles (201).

Yellow Toner Particles

Production Example 2

The procedure in Yellow Toner Particles Production Example 1 was repeated except that the pigment dispersion (101) was changed for the pigment dispersions (102) to (136), to obtain yellow toner particles (202) to (236), respectively.

Comparative Yellow Toner Particles

Production Example 1

The procedure in Yellow Toner Particles Production Example 1 was repeated except that the pigment dispersion (101) was changed for the pigment dispersions (139) to (141), (144) and (145), to obtain yellow toner particles (237) to (241), respectively, for comparison.

Yellow Toner

Production Example 1

In 100.00 parts of the yellow toner particles (201) obtained, 1.80 parts of hydrophobic-treated fine silica powder with 200 $m^2/g$ of specific surface area as measured by BET method was dry-process mixed by means of Henschel mixer (manufactured by Nippon Coke & Engineering Co., Ltd.) to obtain a yellow toner (301).

Yellow Toner

Production Example 2

The procedure in Yellow Toner Production Example 1 was repeated except that the yellow toner particles (201) were changed for the yellow toner particles (202) to (236), to obtain yellow toners (302) to (336), respectively.

Comparative Yellow Toner

Production Example 1

The procedure in Yellow Toner Production Example 1 was repeated except that the yellow toner particles (201) were changed for the yellow toner particles (237) to (241), to obtain yellow toners (337) to (341), respectively, for comparison.

Example 3

The yellow toners obtained in the present invention were evaluated in the following way.
Yellow Toner, Color Tone Evaluation
About the yellow toners (301) to (336), 5 parts of each yellow toner was blended with 95.00 parts of a ferrite carrier coated with acrylic resin, to make up developers. Using a conversion machine of a color copying machine CLC-1100 (manufactured by CANON INC.; a fixing oil application mechanism was removed), images were reproduced in an environment of temperature 25° C./humidity 60% RH, and $L^*$ and $C^*$ in the $L^*a^*b^*$ color system as prescribed by CIE (Commission Internationale de l'Eclairage, Paris) were measured with a reflection densitometer SPECTROLINO (manufactured by Gretag Macbeth Holding AG) under conditions of light source: D50 and visual field: 2°. On the basis of images formed using a yellow toner not containing any pigment dispersant, the percentages of improvement in $C^*$ at $L^*=95.5$ of the images formed using the respective yellow toners were evaluated as shown below.

A: The percentage of improvement in $C^*$ is 5% or more.
B: The percentage of improvement in $C^*$ is 1% or more to less than 5%.
C: The percentage of improvement in $C^*$ is 0% or more to less than 1%.
D: The percentage of improvement in $C^*$ is less than 0%.

The color tone was judged to be good as long as the percentage of improvement in $C^*$ is 1% or more.

The types of yellow toners and the results of evaluation of color tones of images formed using the yellow toners are shown in Table 8.

Comparative Example 2

The yellow toners (337) to (341) for comparison were evaluated in the same way as in Example 3. The results of evaluation are shown in Table 8.

TABLE 8

| Color Tone Evaluation Results of Yellow Toners | |
| --- | --- |
| Yellow toner | Color tone |
| 301 | B |
| 302 | A |
| 303 | A |
| 304 | A |
| 305 | A |
| 306 | A |
| 307 | A |
| 308 | B |
| 309 | B |
| 310 | B |
| 311 | B |
| 312 | B |
| 313 | B |
| 314 | B |
| 315 | B |
| 316 | B |
| 317 | B |
| 318 | B |
| 319 | B |
| 320 | B |
| 321 | A |
| 322 | A |
| 323 | A |
| 324 | B |
| 325 | B |
| 326 | A |
| 327 | A |
| 328 | A |
| 329 | A |
| 330 | A |
| 331 | A |
| 332 | A |
| 333 | A |
| 334 | B |
| 335 | B |
| 336 | B |
| 337 | D |
| 338 | D |
| 339 | D |
| 340 | D |
| 341 | D |

As is seen from Table 8, the azo compound of the present invention affords toners that afford a good color tone. From this fact, it has been ascertained that the azo compound of the present invention is useful as an azo pigment dispersant for toners.

INDUSTRIAL APPLICABILITY

As examples of application of the present invention, the azo compound according to the present invention is applicable in various uses, and, without limitations to its uses as the pigment dispersant described in the present specification, it is also usable in colorants for toners for developing electrostatically charged images, colorants for ink-jet recording inks, colorants for thermal transfer recording sheets, colorants for color filters, and colorants for optical recording mediums.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-190238, filed Aug. 27, 2010, which is hereby incorporated by reference herein in its entirety.

The invention claimed is:

1. An azo compound represented by formula (1):

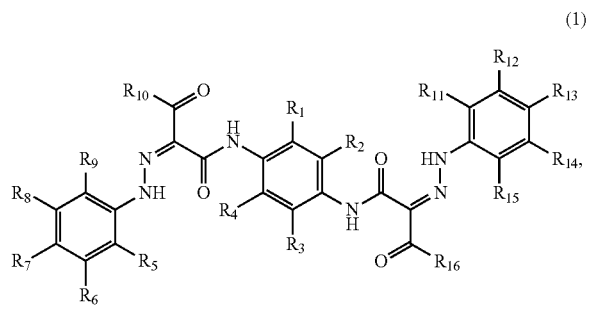

wherein $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $CONR_{18}R_{19}$ group, where $R_{17}$ represents a hydrogen atom or an alkyl group having 1 to 3 carbon atom(s), $R_{18}$ represents a methyl group, and $R_{19}$ represents a hydrogen atom or a methyl group; $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group.

2. The azo compound according to claim 1, wherein $R_{10}$ and $R_{16}$ in the formula (1) are all methyl groups.

3. The azo compound according to claim 1, wherein, in the formula (1), $R_5$ and $R_8$ are all $COOR_{17}$ groups and $R_6$, $R_7$ and $R_9$ are all hydrogen atoms.

4. The azo compound according to claim 1, wherein, in the formula (1), at least one of $R_5$ to $R_9$ is the $COOR_{17}$ group, where $R_{17}$ is a methyl group.

5. The azo compound according to claim 1, wherein, in the formula (1), at least one of $R_{11}$ to $R_{15}$ is the $L_1R_{20}$ group, where $L_1$ is:

a carboxylate group

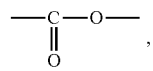

a carboxylic acid secondary amide group

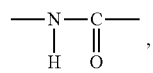

a sulfonate group

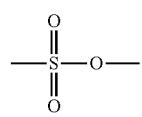

or
a sulfonic acid secondary amide group

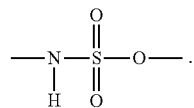

6. The compound according to claim 1, wherein a total sum of carbon atoms of all $R_{20}$ to $R_{22}$ in the $L_1R_{20}$ group and $L_2R_{21}R_{22}$ group the formula (1) has is 10 or more.

7. An azo compound represented by formula (1):

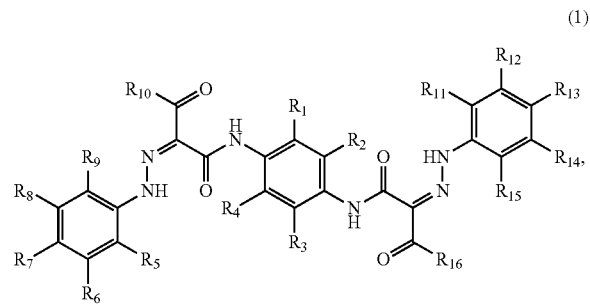

wherein $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $COOR_{17}$ group or the $CONR_{18}R_{19}$ group, where $R_{17}$ to $R_{19}$ each represent a hydrogen atom or an alkyl group having 1 to 3 carbon atom(s); $R_{10}$ represents an alkyl group having 1 to 6 carbon atom(s) or a phenyl group; $R_{11}$ to $R_{15}$ each represent a hydrogen atom or an $L_2R_{21}R_{22}$ group, and at least one of $R_{11}$ to $R_{15}$ represents the $L_2R_{21}R_{22}$ group, where $L_2$ represents a carboxylic acid tertiary amide group

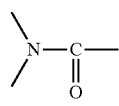

or a sulfonic acid tertiary amide group

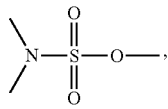

and wherein $R_{21}$ and $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group.

8. A pigment dispersant which comprises a compound represented by formula (1):

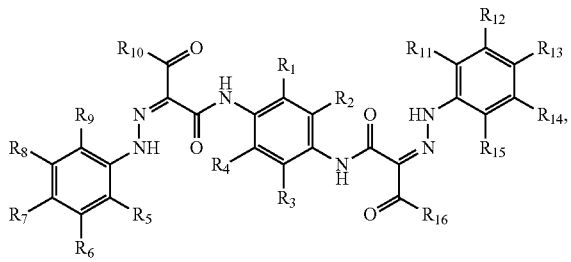

wherein $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $CONR_{18}R_{19}$ group, where $R_{17}$ represents a hydrogen atom or an alkyl group having 1 to 3 carbon atom(s), $R_{18}$ represents a methyl group, and $R_{19}$ represents a hydrogen atom or a methyl group; $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group.

9. A pigment composition which comprises a pigment dispersant according and an azo pigment, wherein the pigment dispersant comprises a compound represented by formula (1):

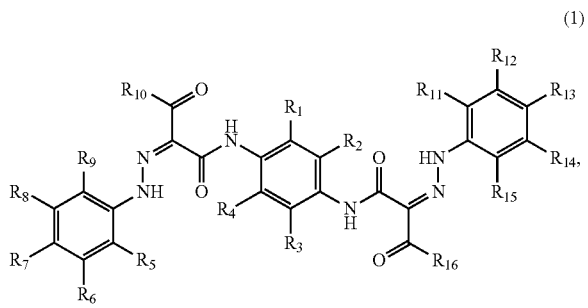

wherein $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $COOR_{17}$ group or the $CONR_{18}R_{19}$ group, where $R_{17}$ to $R_{19}$ each represent a hydrogen atom or an alkyl group having 1 to 3 carbon atom(s); $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group, and wherein the azo pigment is a compound represented by formula (2):

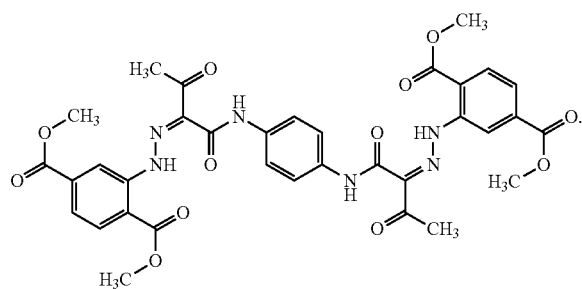

10. A toner which comprises toner particles having a binder resin and a colorant, the colorant comprising the pigment composition according to claim 9.

11. A pigment dispersion which comprises a pigment composition containing a pigment dispersant, an azo pigment, and a non-water-soluble solvent, wherein the pigment dispersant comprises a compound represented by formula (1):

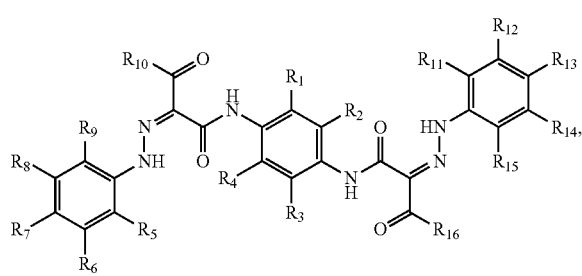

wherein $R_1$ to $R_4$ each represent a hydrogen atom or a halogen atom; $R_5$ to $R_9$ each represent a hydrogen atom, a $COOR_{17}$ group or a $CONR_{18}R_{19}$ group, and at least one of $R_5$ to $R_9$ represents the $COOR_{17}$ group or the $CONR_{18}R_{19}$ group, where $R_{17}$ to $R_{19}$ each represent a hydrogen atom or an alkyl group having 1 to 3 carbon atom(s); $R_{10}$ represents an alkyl group having 1 to 6 carbon atom(s) or a phenyl group; $R_{11}$ to $R_{15}$ each represent a hydrogen atom, an $L_1R_{20}$ group or an $L_2R_{21}R_{22}$ group, and at least one of $R_{11}$ to $R_{15}$ represents the $L_1R_{20}$ group or the $L_2R_{21}R_{22}$ group, where $L_1$ represents a divalent linking group, $L_2$ represents a trivalent linking group, and $R_{20}$ to $R_{22}$ each represent an alkyl group having 8 or more carbon atoms or an alkenyl group having 8 or more carbon atoms; and $R_{16}$ represents an alkyl group having 1 to 6 carbon atom(s) or a phenyl group, and
wherein the non-water-soluble solvent is styrene.

* * * * *